US007041851B2

(12) United States Patent
Kung et al.

(10) Patent No.: US 7,041,851 B2
(45) Date of Patent: May 9, 2006

(54) FLUORINATED PHENYL THIOPHENYL DERIVATIVES AND THEIR USE FOR IMAGING SEROTONIN TRANSPORTERS

(75) Inventors: Hank F. Kung, Wynnewood, PA (US); Chyng-Yann Shiue, Villanova, PA (US); Shunichi Oya, Princeton Junction, NJ (US); Seok Rye Choi, Drexel Hill, PA (US); Grace G. Shiue, Villanova, PA (US); Ping Fang, Drexel Hill, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 82 days.

(21) Appl. No.: 10/388,363

(22) Filed: Mar. 14, 2003

(65) Prior Publication Data
US 2003/0236234 A1    Dec. 25, 2003

Related U.S. Application Data

(60) Provisional application No. 60/364,905, filed on Mar. 14, 2002.

(51) Int. Cl.
C07C 321/28    (2006.01)
C07C 321/30    (2006.01)
A61K 31/10    (2006.01)

(52) U.S. Cl. ...................... 564/341; 514/612; 514/649; 514/653

(58) Field of Classification Search ................ 514/612, 514/649, 653; 564/341
See application file for complete search history.

(56) References Cited

FOREIGN PATENT DOCUMENTS

| EP | 0 402 097 A1 | 12/1990 |
| EP | 0 282 944 B1 | 11/1996 |
| GB | 1 207 725 | 10/1970 |
| WO | WO 93/12080 A1 | 6/1993 |
| WO | WO 97/17325 A1 | 5/1997 |
| WO | WO 03/096978 A2 | 11/2003 |

OTHER PUBLICATIONS

Acton, P.D., et al., "Single-photon emission tomography imaging of serotonin transporters in the non-human primate brain with the selective radioligand [$^{123}$I] IDAM," *Eur. J. Nucl. Med.* 26:854-861, Springer-Verlag (1999).

Acton, P.D., et al., "Single-photon emission tomography imaging of serotonin transporters in the non-human primate brain with [$^{123}$I]ODAM," *Eur. J. Nucl. Med.* 26:1359-1362, Springer-Verlag (1999).

Acton, P.D., et al., "Quantification of Serotonin Transporters in Nonhuman Primates Using [$^{123}$I]ADAM and SPECT," *J. Nucl. Med.* 42:1556-1562, Society of Nuclear Medicine (Oct. 2001).

Angelini, G., et al., "New developments in the synthesis of no-carrier-added (NCA) $^{18}$F-labeled aryl fluorides using the nucleophilic aromatic substitution reaction," *J. Labelled Cpd. Radiopharm.* 21:1223-1225, John Wiley & Sons, Ltd. (1984).

Angelini, G., et al., "Nucleophilic aromatic substitution of activated cationic groups by $^{18}$F-labeled fluoride. A useful route to no-carrier-added (NCA) $^{18}$F-labeled aryl fluorides," *J. Fluor. Chem.* 27:177-191, Elsevier Sequoia (1985).

Attiná, "Displacement of a Nitro-group by [$^{18}$F]Fluoride Ion. A New Route to Aryl fluorides of High Specific Activity, " *J. Chem. Soc. Chem. Commun.* No. 3, 108-109, Royal Society of Chemistry, London (1983).

Attinà, M., et al., "Labeled aryl fluorides from the nucleophilic displacement of activated nitro groups by $^{18}$F-F$^-$, "*J. Labelled Cpd. Radiopharm.* 20:501-514, John Wiley & Sons, Ltd., (1983).

Bergström, K.A., et al., "In vitro and in vivo characterisation of nor-β-CIT: a potential radioligand for visualisation of the serotonin transporter in the brain," *Eur. J. Nucl. Med.* 24:596-601, Springer-Verlag (1997).

Berridge, M.S., et al., "Aromatic fluorination with N.C.A. F-18 fluoride: A comparative study," *J. Labelled Cpd. Radiopharm.* 22:687-694, John Wiley & Sons, Ltd. (1985).

Biegon, A., et al., "[$^{125}$I]5-Iodo-6-nitroquipazine: a potent and selective ligand for the 5-hydroxytryptamine uptake complex. II. In vivo studies in rats, *Brain Res.* 619:236-246, Elsevier Science Publishers B.V. (1993).

Blough, B.E., et al., "3β-(4-Ethyl-3-iodophenyl)nortropane-2β-carboxylic Acid Methyl Ester as a High-Affinity Selective Ligand for the Serotonin Transporter," *J. Med. Chem.* 40:3861-3864, American Chemical Society (1997).

Buck, A., et al., Evaluation of Serotonergic Transporters Using PET and [$^{11}$C] (+)McN-5652: Assessment of Methods, *J. Cereb. Blood Flow Metab.* 20:253-262, Lippincott Williams & Wilkens (2000).

Choi, S-R., et al., "Selective In Vitro and In Vivo Binding of [$^{125}$I]ADAM to Serotonin Transporters in Rat Brain," *Synapse* 38:403-412, Wiley-Liss, Inc. (2000).

(Continued)

*Primary Examiner*—Brian Davis
(74) *Attorney, Agent, or Firm*—Sterne, Kessler, Goldstein & Fox P.L.L.C.

(57) ABSTRACT

This invention relates to novel fluorinated phenyl thiphenyl (also named diarylsulfide) derivatives and their use in Positron Emission Tomagraphy (PET) imaging of Serotonin Transporters (SERTS). The present invention also provides diagnostic compositions comprising the novel compounds of the present invention, and a pharmaceutically acceptable carrier or diluent. The invention further provides a method of imaging SERTS, comprising introducing into a patient a detectable quantity of a labeled compound of the present invetion, or a pharmaceutically acceptable salt, ester, amide or prodrug thereof.

21 Claims, 1 Drawing Sheet

OTHER PUBLICATIONS

Choi, S-R., et al., "Structure-activity relationship of analogs of ADAM as ligands for serotonin transporters," *J. Labelled Cpd. Radiopharm. 44 (Suppl. 1)*:S190-S192, John Wiley & Sons, Ltd. (May 2001).

Chumpradit, S., et al., "Iodinated Tomoxetine Derivatives as Selective Ligands for Serotonin and Norepinephrine Uptake Sites," *J. Med. Chem.* 35:4492-4497, American Chemical Society (1992).

Constantinou, M., et al., "Radiofluoridations of m-substituted nitrobenzenes," *J. Labelled Cpd. Radiopharm. 44 (Suppl. 1)*:S889-S891, John Wiley & Sons, Ltd. (May 2001).

Coryell, W., "The Treatment of Psychotic Depression," *J. Clin. Psychiatry 59 (Suppl. 1)*:22-27, Physicians Postgraduate Press (1998).

D'Amato, R.J., et al., "Selective Labeling of Serotonin Uptake Sites in Rat Brain by [$^3$H]Citalopram Contrasted to Labeling of Multiple Sites by [$^3$H]Imipramine," *Pharmacol. Exp. Ther.* 242:364-371, The Williams & Wilkins Company (1987).

Das, M.K., and Mukherjee, J., "Radiosynthesis of [F-18] Fluoxetine as a Potential Radiotracer for Serotonin Reuptake Sites," *Appl. Radiat. Isot.* 44:835-842, Pergamon Press, Ltd. (1993).

Douglass, I.B., and Farah, B.S., "The Anhydrous Chlorination of Some Mercapto Acids and Analogous Disulfides$^{1,2,3}$," *J. Org. Chem.* 26:351-354, American Chemical Society (1961).

Drouin, J., et al., "Reduction of Nitrobenzene with Sodium Borohydride-Copper(II) Sulfate System: A Reinvestigation, " *SYNLETT* 9:791-793, Thieme (1993).

Elfving, B., et al., "Binding Characteristics of Selective Serotonin Reuptake Inhibitors With Relation to Emission Tomography Studies," *Synapse* 41:203-211, Wiley-Liss, Inc. (Sep. 2001).

Emond, P., et al., "Substituted Diphenyl Sulfides as Selective Serotonin Transporter Ligands: Synthesis and In Vitro Evaluation," *J. Med. Chem.* 45:1253-1258, American Chemical Society (Published on Web Feb. 9, 2002).

Ferris, R.M. et al., "Pharmacological Properties of 403U76, a New Chemical Class of 5-Hydroxytryptamine- and Noradrenaline- reuptake Inhibitor," *J. Pharm. Pharmacol.* 47:775-781, Pharmaceutical Press (1995).

Frazer, A., and Hensler, J.G., "5-HT$_{1A}$ Receptors and 5-HT$_{2A}$-Mediated Responses: Effect of Treatments That Modify Serotonergic Neurotransmission," *Ann. NY Acad. Sci.* 600:460-475, New York Academy of Sciences (1990).

Frazer, A., "Antidepressants," *J. Clin. Psychiatry 58 (Suppl. 6)*:9-25, Physicians Postgraduate Press (1997).

Frazer, A., "Serotonergic and Noradrenergic Reuptake Inhibitors: Prediction of Clinical Effects From In Vitro Potencies," *J. Clin. Psychiatry 62 (Suppl. 12)*:16-23, Physicians Postgraduate Press (Jun. 2001).

Fujita, M., et al., "Differential kinetics of [$^{123}$I]β-CIT binding to dopamine and serotonin transporters," *Eur. J. Nucl. Med.* 23:431-436, Springer-Verlag (1996).

Fuller, R.W., "Serotonin uptake inhibitors: Uses in clinical therapy and in laboratory research," *Prog. Drug Res.* 45:167-204, Birkhäuser Verlag (1994).

Ginovart, N., et al., "Positron Emission Tomography Quantification of [$^{11}$C]-DASB Binding to the Human Serotonin Transporter: Modeling Strategies," *J. Cereb. Blood Flow Metab.* 21:1342-1353, Lippincott Williams & Wilkins, Inc. (Nov. 2001).

Gozlan, H., and Hamon, M., "Pharmacology and molecular biology of central 5-HT receptors," in *Anxiety: Neurobiology, Clinic and Therapeutic Perspectives* 232:141-150, INSERM/John Libbey Eurotext, Ltd. (1993).

Habert, E., et al., "Characteristization of [$^3$H]paroxetine binding to rat cortical membranes," *Eur. J. Pharmacol.* 118:107-114, Elsevier (1985).

Halldin, C., et al., "$^{11}$CMADAM—a selective radioligand for PET-examination of the serotonin transporter in the monkey brain," *J. Nucl. Med. 42 (Suppl.)*:112P, Abstract No. 419, Society of Nuclear Medicine (Jun. 2001).

Halldin, C., "A PET-comparison in monkey brain of $^{11}$C-MADAM labeled in two different positions—selective for the serotonin transporter," *J. Nucl. Med. 43 (Suppl.)*:164P, Abstract No. 596, Society of Nuclear Medicine (Jun. 2002).

Hammadi, A., and Crouzel, C., "Synthesis of $^{18}$F-labeled fluoxetine: A selective serotonin uptake inhibitor," *J. Labelled Cpd. Radiopharm.* 32:305-306, Wiley-Liss (1993).

Harvey, B.H., "The neurobiology and pharmacology of depression. A comparative overview of serotonin selective antidepressants," *S. Afr. Med. J.* 87:540-550, South African Medical Association (1997).

Hashimoto, K., et al., "Synthesis and evaluation of [$^{11}$C] cyanoimipramine," *Int. J. Radiat. Appl. Instrum. [B], Nucl. Med. Biol.* 14:587-592, Permagon Journals, Ltd. (1987).

Hashimoto, K., and Goromaru, T., "High-affinity [$^3$H]6-nitroquipazine binding to the 5-Hydroxytryptamine transport system in rat lung," *Biochem. Pharmacol.* 41:1679-1682, Pergamon Press (1991).

Hashimoto, K., and Goromaru, T., "High affinity binding of [$^3$H]6-nitroquipazine to cortical membranes in the rat: Inhibition by 5-hydroxytryptamine and 5-hydroxytryptamine uptake inhibitors," *Neuropharmacology* 30:113-117, Pergamon Press (1991).

Heninger, G.R. et al., "The Revised Monoamine Theory of Depression: A Modulatory Role for Monoamines, Based on New Findings From Monoamine Depletion Experiments in Humans," *Pharmacopsychiatry* 29:2-11, Georg Thieme Verlag Stuttgart (1996).

Hiltunen, J., et al., "Iodine-123 labeled nor-β-CIT as a potential tracer for serotonin transporter imaging in the human brain with single-photon emission tomography," *Eur. J. Nucl. Med.* 25:19-23, Springer-Verlag (1998).

Holliday, S.M., and Plosker, G.L., "Paroxetine: A Review of its Pharmacology, Therapeutic Use in Depression and Therapeutic Potential in Diabetic Neuropathy," *Drug Aging* 3:278-299, Adis International, Ltd. (1993).

Houle, S., et al., "Imaging the serotonin transporter with positron emission tomography: initial human studies with [$^{11}$C]DAPP and [$^{11}$C]DASB," *Eur. J. Nucl. Med.* 27:1719-1722, Springer-Verlag (2000).

Huang, Y., et al., "Fluorinated Analogues of ADAM as New PET Radioligands for the Serotonin Transporter: Synthesis and Pharmacological Evaluation," *J. Labelled Cpd. Radiopharm. 44 (Suppl. 1)*:S18-S20, John Wiley & Sons (May 2001).

Huang, Y., et al., "Synthesis and characterization of a new PET ligand for the serotonin transporter: $^{11}$C5-bromo-2-{2-[9dimethylamino)methyl]phe-nylsulfanyl}phenylamine," *J. Nucl. Med.* 42:112P-113P, Abstract No. 420, Society of Nuclear Medicine (Jun. 2001).

Huang, Y., et al., "Radiosynthesis and evaluation of [$^{18}$F] AFM, a selective PET tracer for the serotonin transporter," *J. Nucl. Med. 43 (Suppl.)*:358P, Abstract No. 1440, Society of Nuclear Medicine (Jun. 2002).

Hume, S.P., et al., "IX-19. Sertraline and paroxetine fail tests in vivo as 5-HT reuptake site ligands for PET," *J. Cereb. Blood Flow Metab.* 9 (*Suppl. 1*):S117, Raven Press (1989).

Hume, S.P., et al., Evaluation of S-[$^{11}$C]Citalopram as a Radioligand for *In Vivo* Labelling of 5-Hydroxytryptamine Uptake Sites, *Int. J. Radiat. Appl. Instrum. B, Nucl. Med. Biol.* 19:851-855, Pergamon Press, Ltd. (1992).

Hyttel, J., "Pharmacological characterization of selective serotonin reuptake inhibitors (SSTIs)," *Int. J. Clin. Psychopharmacol.* 9 (*Suppl. 1*):19-26, Rapid Communications of Oxford, Ltd. (1994).

Jagust, W.J., et al., "Iodine-123-5-Iodo-6-Nitroquipazine: SPECT Radiotracer to Image the Serotonin Transporter," *J. Nucl. Med.* 37:1207-1214, Society of Nuclear Medicine (1996).

Jarkas, N., et al., "Synthesis of new fluoroalkyl derivatives of ADAM, potential radiotracers for mapping serotonin transporters (SERT) by PET," *4th Intl. Symposium on Radiohalogens*, Sep. 9-13, 2000, Whistler, B.C., Canada, (2000).

Jarkas, N., et al., "Synthesis and radiolabeling of new derivatives of ADAM, potential candidates as SERT imaging agents for PET," *J. Labelled. Cpd. Radiopharm.* 44 (*Suppl. 1*):S204-S206, John Wiley & Sons (May 2001).

Jarkas, N., et al., "Radiolabeling and *in vivo* characterization of $^{11}$C-EADAM: an attractive PET radioligand for serotonin transporters (SERT)," *J. Nucl. Med.* 43 (*Suppl.*):164P, Abstract No. 597, Society of Nuclear Medicine (Jun. 2002).

Jflek, J., et al., "Potential antidepressants: 2-(methoxy- and hydroxy-phenylthio)benzylamines as selective inhibitors of 5-hydroxytryptamine re-uptake in the brain," *Collect. Czech. Chem. Commun.* 54:3294-3338, Nakladatelstvi Ceskoslovenski Akademie Ved (1989).

Kilbourn, M.R., et al., "Synthesis of radiolabeled inhibitors of presynaptic monoamine uptake systems: [$^{18}$F]GBR 13119 (DA), [$^{11}$C]nisoxetine (NE), and [$^{11}$C] fluoxetine (5-HT)," *J. Labelled. Cpd. Radiopharm.* 26: 412-414, John Wiley & Sons (1989).

Kudo, N., et al., "A Novel Synthesis of 4*H*-1,4-Benzoxazines," *Chem Pharm. Bull.* 44:1663-1668, Pharmaceutical Society of Japan (1996).

Kuikka, J.T., et al., "Comparison of iodine-123 labelled 2β-carbomethoxy-3β-(4-iodophenyl)tropane and 2β-carbomethoxy-3β-(4-iodophenyl)-*N*-(3-fluoropropyl) nortropane for imaging of the dopamine transporter in the living human brain," *Eur. J. Nucl. Med.* 22:356-360, Spriner-Verlag (1995).

Kung, M-P., et al., "4-Iodotomoxetine: a novel ligand for serotonin uptake sites," *Life Sci.* 51:95-106, Pergamon Press, Ltd. (1992).

Kung, M-P., et al., "IPT: A Novel Iodinated Ligand for the CNS Dopamine Transporter," *Synapse* 20:316-324, Wiley-Liss, Inc. (1995).

Kung, M-P., et al., "Characterization of [$^{123}$I]IDAM as a novel single-photon emission tomography tracer for serotonin transporters," *Eur. J. Nucl. Med.* 26:844-853, Springer-Verlag (1999).

Laruelle, M., et al., "SPECT Imaging of Dopamine and Serotonin Transporters with [$^{123}$I]β-CIT: Pharmacological Characterization of Brain Uptake in Nonhuman Primates," *Synapse* 13:295-309, Wiley-Liss (1993).

Laruelle, M., et al., "Dopamine and Serotonin Transporters in Patients with Schizophrenia: An Imaging Study with [$^{123}$I]β-CIT," *Biol. Psychiatry* 47:371-379, Elsevier (2000).

Lasne, M.-C., et al., "The Radiosynthesis of [*N-methyl*-$^{11}$C]-Sertraline," *Int. J. Radiat. Appl. Instrum. [A] Appl. Rad. Isot.* 40:147-151, Pergamon Press (1989).

Malison, R.T., et al., "Reduced Brain Serotonin Transporter Availability in Major Depression as Measured by [$^{123}$I]-2β-carbomethoxy-3β-(4-iodophenyl)tropane and Single Photon Emission Computed Tomography," *Biol. Psychiatry* 44:1090-1098, Elsevier (1998).

Mann, J.J., et al., "The neurobiology of suicide," *Nat. Med.* 4:25-30, Nature Publishing Group (1998).

Mann, J.J., et al., "A Serotonin Transporter Gene Promoter Polymorphism (5-HTTLPR) and Prefrontal Cortical Binding in Major Depression and Suicide," *Arch. Gen. Psychiatry* 57:729-738, American Medical Association (2000).

Maryanoff, B.E., et al., "Pyrroloisoquinoline Antidepressants. 3. A Focus on Serotonin," *J. Med. Chem.* 33:2793-2797, American Chemical Society (1990).

Mathis, C.A., et al., "[$^{125}$I]5-Iodo-6-nitro-2-piperazinylquinoline: a potent and selective ligand for the serotonin uptake complex," *Eur. J. Pharmacol.* 210: 103-104, Elsevier Science Publishers B.V. (1992).

Mathis, C.A., et al., "[$^{125}$I]5-Iodo-6-nitroquipazine: a potent and selective ligand for the 5-hydroxytryptamine uptake complex. I. In vitro studies," *Brain Res.* 619:229-235, Elsevier Science Publishers B.V. (1993).

Meltzer, c.C., et al., "Serotonin in Aging, Late-Life Depression, and Alzheimer's Disease: The Emerging Role of Functional Imaging," *Neuropsychopharmacology* 18:407-430, Elsevier Science, Inc. (1998).

Meyer, J.H., et al., "Lower dopamine transporter binding potential in striatum during depression, " *Neuroreport* 12: 4121-4125, Lippincott Williams & Wilkins (Dec. 2001).

Meyer, J.H., et al., "Occupancy of Serotonin Transporters by Paroxetine and Citalopram During Treatment of Depression: A [$^{11}$C]DASB PET Imaging Study," *Am. J. Psychiatry* 158:1843-1849, American Psychiatric Association (Nov. 2001).

Mishani, E., et al., "A study of α,α,α-Trifluorotoluenes Mediated [$^{18}$F]Fluoro-for-Nitro Exchange. A Useful Intermediate in the Synthesis of Highly Fluorinated Radiopharmaceuticals," *J. Labelled Comp. Radiopharm.* 37:575-577, John Wiley & Sons (1995).

Moody, C.J., and Pitts, M.R., "Indium as a Reducing Agent: Reduction of Aromatic Nitro Groups," *Synlett* 9:1028, Thieme (1998).

McCann, U.D., et al., "Positron emission tomographic evidence of toxic effect of MDMA ("Ecstasy") on brain serotonin neurons in human beings," *Lancet* 352:1433-1437, Lancet Publishing Group (1998).

Okachi, R., et al., "Synthesis and Antibacterial Activity of 2,2'-Dithiobis(benzamide) Derivatives against *Myobacterium* Species," *J. Med. Chem.* 28:1772-1779, American Chemical Society (1985).

Owens, M.J., and Nemeroff, C.B., "Role of Serotonin in the Pathophysiology of Depression: Focus on the Serotonin Transporter," *Clin. Chem.* 40:288-295, American Association For Clinical Chemistry (1994).

Oya, S., et al., "A New Single-Photon Emission Computed Tomography Imaging Agent for Serotonin Transporters: [$^{123}$I]IDAM, 5-Iodo-2-((2-((dimethylamino)methyl) phyenyl)thio)benzyl Alcohol," *J. Med. Chem.* 42:333-335, American Chemical Society (1999).

Oya, S., et al., "2-((2-((Dimethylamino)methyl)phenyl) thio)-5-iodophenylamine (ADAM): An Improved Serotonin Transporter Ligand," *Nucl. Med. Biol.* 27:249-254, Elsevier Science, Inc. (2000).

Oya, S., et al., "Synthesis and characterization of $^{18}$F-IDAM as PET imaging agent for serotonin transporters," *J. Labelled Cpd. Radiopharm.* 44 (*Suppl. 1*):S15-S17, John Wiley & Sons (May 2001).

Oya, S., et al., "A fluorinated ADAM derivative as a serotonin transporter imaging agent," *J. Nucl. Med.* 43 (*Suppl.*):165P, Abstract No. 600, Society of Nuclear Medicine (Jun. 2002).

Oya, S., et al., "New PET Imaging Agent for the Serotonin Transporter: [18$^F$]ACF (2-[(2-Amino-4-chloro-5-fluorophenyl)thio]-*N, N*-dimethyl-benzenmethanamine)," *J. Med. Chem.* 45:4716-4723, American Chemical Society (Published on Web Sep. 5, 2002).

Parsey, R.V., et al., "In Vivo Quantification of Brain Serotonin Transporters in Humans Using [$^{11}$C]McN 5652," *J. Nucl. Med.* 41:1465-1477, Society of Nuclear Medicine (2000).

Perry, E.K., et al., "Decreased Imipramine Binding in the Brains of Patients with Depressice Illness," *Br. J. Psychiat.* 142:188-192, Royal College of Psychiatrists (1983).

Pirker, W., et al., "β-CIT SPECT demonstrates blockade of 5HT-uptake sites by citalopram in the human brain in vivo," *J. Neural. Transm. [Gen. Sect.]* 100:247-256, Springer-Verlag (1995).

Raisman, R., et al., "High-affinity $^3$H-imipramine binding in rat cerebral cortex," *Eur. J. Pharmacol.* 54:307-308, Elsevier/North-Holland Biomedical Press (1979).

Ricaurte, G.A., et al., "toxicodynamics and long-term toxicity of the recreational drug, 3,4-methylenedioxymethamphetamine (MDMA, 'Ecstasy')," *Toxicol. Lett.* 112-113:143-146, Elsevier Science Ireland, Ltd. (2000).

Sasson, Y., et al., "Tetramethylammonium chloride as a selective and robust phase transfer catalyst in a solid-liquid halex reaction: the role of water," *Chem. Commun.* 3:297-298, The Royal Society of Chemistry (1996).

Scheffel, U., et al., "Evaluation of 11C-citalopram and 11-C-fluoxetine as *in vivo* ligands for the serotonin uptake site," *J. Nucl. Med.* (*Suppl.*) 31:883, Abstract No. 759, Society for Nuclear Medicine (1990).

Scheffel, U., et al., "Development of PET/SPECT Ligands for the Serotonin Transporter," *NIDA Res. Monogr.* 138:111-130, National Institute on Drug Abuse (1994).

Schindlbauer, H., "Reactions with dimethylformamide. I. Synthesis of carboxylic acid dimethylamides," *Monatsh. Chem.* 99:1799-1807, Springer-Verlag Wien (1968).

Shiue, C-Y., et al., "Application of the Nucleophilic Substitution Reaction to the Synthesis of No-Carrier-Added [$^{18}$F]Fluorobenzene and Other $^{18}$F-Labeled Aryl Fluorides," *J. Labelled Cpd. Radiopharm.* 21:533-547, John Wiley & Sons, Ltd. (1984).

Shiue, C-Y., et al., "PET Study of the Distribution of [$^{11}$C]Fluoxetine in a Monkey Brain," *Nucl. Med. Biol.* 22:613-616, Elsevier Science, Ltd. (1995).

Shiue, C., et al., "5-Iodo-2-[[2,2-[([$^{11}$C]dimethyl-amino) methyl]phenyl]thio]benzyl alcohol (N-[$^{11}$C]IDAM) : A new serotonin re-uptake sites tracer for PET studies," *J. Nucl. Med.* 41 (*Suppl.*):241P, Abstract No. 1064, Society of Nuclear Medicine (2000).

Shiue, G.G., et al., "Synthesis of N,N-dimethyl-2-(2-amino-4-$^{18}$F-flu-orophenylthio)benzylamine as a serotonin transporter imaging agent," *J. Nucl. Med.* 43 (*Suppl.*):165P, Abstract no. 601, Society of Nuclear Medicine (May 2002).

Shuie, G.G., et al., "Synthesis of *N,N*-dimethyl-2-(2-amino-4-[$^{18}$F] fluorophenylthio)benzylamine as a serotonin transporter imaging agent," *Appl. Radiat. Isot.* 58: 183-191, Elsevier Science, Ltd. (Feb. 2003).

Soudijn, W., and van Wijngaarden, I., "5-HT Transporter," in *Serotonin Receptors and their Ligands*, vol. 27, Olivier, B., et al., eds., Elsevier Science B.V., Amsterdam, The Netherlands, pp. 327-361 (1997).

Staley, J.K., et al., "Imaging of the Serotonergic System: Interactions of Neuroanatomical and Functional Abnormalities of Depression," *Biol. Psychiatry* 44:534-549, Elsevier (1998).

Suehiro, M., et al., "Radiosynthesis and Evaluation of N-(3-[$^{18}$F]Fluoropropyl)-paroxetine as a Radiotracer for *In Vivo* Labeling of Serotonin Uptake Sites by PET," *Int. J. Radiat. Appl. Instum. [B], Nucl. Med. Biol.* 18:791-796, Pergamon Press (1991).

Suehiro, M., et al., "Synthesis of a Radiotracer for Studying Serotonin Uptake Sites with Positron Emission Tomography: [$^{11}$C]McN-5652-Z," *J. Labelled Cpd. Radiopharm.* 31:841-848, John Wiley & Sons, Ltd. (1992).

Suehiro, M., et al., "[$^{11}$C](+)McN5652 as a radiotracer for imaging serotonin uptake sites with PET," *Life Sci.* 53:883-892, Pergamon Press, Ltd. (1993).

Suehiro, M., et al., "A PET Radiotracer for Studying Serotonin Uptake Sites: Carbon-11-McN 5652Z," *J. Nucl. Med.* 34:120-127, Society for Nuclear Medicine (1993).

Suehiro, M., et al., "Highly Potent Indanamine Serotonin Uptake Blockers as Radiotracers for Imaging Serotonin Uptake Sites," *Nucl. Med. Biol.* 21:1083-1091, Elsevier Science, Ltd. (1994).

Suehiro, M., et al., "An Improved Method for the Synthesis of Radiolabeled McN5652 via Thioester Precursors," *Nucl. Med. Biol.* 22:543-545, Elsevier Science, Ltd. (1995).

Suehiro, M., et al., "Radiosynthesis and Biodistribution of the S-[$^{18}$F]Fluoroethyl Analog of McN5652," *Nucl. Med. Biol.* 23:407-412, Elsevier Science, Inc. (1996).

Szabo, Z., et al., "Positron Emission Tomography Imaging of Serotonin Transporters in the Human Brain Using [$^{11}$C](+)McN5652," *Synapse* 20:37-43, Wiley-Liss, Inc. (1995).

Szabo, Z., et al., "Positron emission tomography of 5-HT reuptake sites in the human brain with C-11 McN5652 Extraction of characteristic images by artificial neural network analysis," *Behav. Brain Red.* 73:221-224, Elsevier Science B.V. (1996).

Szabo, Z., et al., "Positron Emission Tomography of 5-HT Transporter Sites in the Baboon Brain with [$^{11}$C]McN5652," *J. Cereb. Blood Metab.* 15:798-805, Lippincott-Raven Publishers (1995).

Szabo, Z., et al., "Impulse-response function and kinetic-model of carbon-11 labeled (+)McN5652," *J. Nucl. Med.* 37 (*Suppl.*):33P, Abstract No. 125, Society of Nuclear Medicine (1996).

Szabo, z., et al., "Kinetic analysis of [$^{11}$C]McN5652: A Serotonin transporter Radioligand," *J. Cereb. Blood Flow Metab.* 19:967-981, Lippincott Williams & Wilkins, Inc. (1999).

Szabo, Z., et al., "Comparison of (+)-$^{11}$C-McN5652 and $^{11}$C-DASB as Serotonin Transporter Radioligands Under Various Experimental Conditions," *J. Nucl. Med.* 43:678-692, Society of Nuclear Medicine (May 2002).

Tauscher, J., et al., "In vivo visualization of serotonin transporters in the human brain during fluoxetine treatment," *Eur. Neuropsychopharmacol.* 9:177-179, Elsevier Science B.V./ECNP. (1999).

Tiihonen, J., et al., "Single-photon emission tomography imaging of monamine transporters in impulsive violent behavior," *Eur. J. Nucl. Med.* 24:1253-1260, Springer-Verlag (1997).

Vercouillie, J., et al., "Precursor synthesis and radiolabelling of [$^{11}$C]ADAM: A potential radioligand for the serotonin transporter exploration by PET," *J. Labelled Cpd. Radiopharm.* 44:113-120, John Wiley & Sons, Ltd. (Feb. 2001).

Willeit, M., et al., "[$^{123}$I]-β-CIT SPECT Imaging Shows Reduced Brain Serotonin Transporter Availability in Drug-Free Depressed Patients with Seasonal Affective Disorder," *Biol. Psychiatry* 47:482-489, Elsevier (2000).

Wilson, A.A., et al., "In vitro and in vivo characterization of [$^{11}$C]-DASB: a probe for in vivo measurements of the serotonin transporter by positron emission tomography," *Nucl. Med. Biol.* 29:509-515, Elsevier Science, Inc. (Jul. 2002).

Wilson, A.A., et al., "Novel Radiotracers for Imaging the Serotonin Transporter by Positron Emission Tomography: Synthesis, Radiosynthesis, and in Vitro and ex Vivo Evaluation of $^{11}$C-Labeled 2-(Phenylthio)araalkylamines," *J. Med. Chem.* 43:3103-3110, American Chemical Society (2000).

Wilson, A.A., and Houle, S., "Radiosynthesis of Carbon-11 Labelled N-Methyl-2-(arlythio)benzylamines: Potential Radiotracers for the Serotonin Reuptake Receptor," *J. Labelled cpd. Radiopharm.* 42:1277-1288, John Wiley & Sons, Ltd. (1999).

Wong, D.T. and Bymaster, F.P., "Development of antidepressant drugs: Fluoxetine (Prozac) and other selective serotonin uptake inhibitors," in *Neurochemistry in Clinical Application*, L.C., and Tang, S.J., eds., Plenum Press, New York, NY, pp. 77-95 (1995).

Zessin, J., et al., "Synthesis of S-([$^{18}$F]fluoromethyl)-(+)-McN5652 as a potential PET radioligand for the serotonin transporter," *Nucl. Med. Biol.* 28:857-863, Elsevier Science, Inc. (Oct. 2001).

Zhuang, Z-P., et al., "A Novel Serotonin Transporter Ligand: (5-Iodo-2-(2-dimethylaminomethylphenoxy)-benzyl Alcohol," *Nucl. Med. Biol.* 27:169-175, Elsevier Science, Inc. (2000).

International Search Report for International Application No. PCT/US03/07935 mailed on Jul. 29, 2003.

Database CAPLUS on STN, Chemical Abstracts (Columbus, Ohio), No. 133:350040, Kung, H.F., "Preparation of agents for serotonin transporter SPECT imaging," abstract of WO 00/66537, Nov. 9, 2000.

Database CAPLUS on STN, Chemical Abstracts (Columbus, Ohio), No. 114:288508, Metha et al., "Preparation of diphenyl sulfides as nervous system agents," abstract of EP 402097, (1990).

Database CAPLUS on STN, Chemical Abstracts (Columbus, Ohio), No. 130:264117, Blin et al., "A New Single-Photon Emission Computed Tomography Imaging Agent for Serotonin Transporters: [123I]IDAM, 5OIodo-2-((2-((dimethylamino)methyl)phenyl)thio) benzyl alcohol," abstract of *J. Med. Chem.* 42:333-335 (1999).

Database CAPLUS on STN, Chemical Abstracts (Columbus, Ohio), No. 108-164322, Blin et al., "[18F] Setoperone: a new high affinity ligand for positron emission tomography study of serotonin-2 receptors in babbon brain in vivo," abstract of *Eur. J. Pharmacol.* 147:73-82 (1988).

Database Caplus on STN, Chemical Abstracts (Columbus, Ohio), No. 125:296229, Suehiro et al., "Radiosynthesis and biodistribution of the S- [18F] fluoroethyl analog of McN5652," abstract of *Nucl. Med. Biol.* 23:407-412 (1996).

2). $R_1=3\text{-}F$, $R_2=H$;     4). $R_1=4\text{-}F$, $R_2=H$;
6). $R_1=R_2=5\text{-}F$;          8). $R_1=4\text{-}CH_3$, $R_2=F$;
10). $R_1=3\text{-}CH_2F$, $R_2=H$;  12). $R_1=4\text{-}CH_2F$, $R_2=H$;
14). $R_1=R_2=5\text{-}CH_2F$.

16). $R_1=3\text{-}F$, $R_2=H$;    18). $R_1=4\text{-}F$, $R_2=H$;
20). $R_1=R_2=5\text{-}F$;         22). $R_1=4\text{-}CH_3$, $R_2=F$;
24). $R_1=3\text{-}CH_2F$, $R_2=H$;  26). $R_1=4\text{-}CH_2F$, $R_2=H$;
28). $R_1=R_2=5\text{-}CH_2F$.

2). $X=H$;     4). $X=F$
6). $X=Cl$;    8). $X=Br$
10). $X=I$;    12). $X=CN$
14). $X=CH_2F$;  16) $X=CH_3$

US 7,041,851 B2

FLUORINATED PHENYL THIOPHENYL DERIVATIVES AND THEIR USE FOR IMAGING SEROTONIN TRANSPORTERS

CROSS-REFERENCE TO RELATED APPLICATION

This application claims the benefit of U.S. Provisional Application No. 60/364,905, filed Mar. 14, 2002.

STATEMENT REGARDING FEDERALLY SPONSORED RESEARCH OR DEVELOPMENT

This invention was made with government support under Grant No. NS35120, awarded by the National Institutes of Health. The government has certain rights in the invention.

BACKGROUND OF THE INVENTION

1. Field of the Invention

This invention relates to novel fluorinated phenyl thiphenyl (also named diarylsulfide) derivatives and their use in Positron Emission Tomography (PET) imaging of Serotonin Transporters.

2. Related Art

Depression, with its related conditions, is one of the most common mental disorders in the United States. It is estimated that about five percent of the adult population experiences a depressive episode in their lifetime that requires antidepressive drug therapy. A chemical in the human brain, called serotonin, has been linked with depression and with other psychiatric disorders such as eating disorders, alcoholism, pain, anxiety and obsessive-compulsive behavior.

Abnormalities in the serotonin transporter (SERT) have been implicated in several neurologic and psychiatric disorders, such as Parkinsonian disorder, depression, suicide, schizophrenia, drug addiction and eating disorders (Mann et al. 2000; Meltzer et al. 1998). In addition, SERT is the primary target for the widely prescribed antidepressant agent (Frazer, 1997). In order to study the above mentioned neurologic and psychiatric disorders, and the mode of action of antidepressant agents in humans, it is of great need to have high affinity and high specificity SERT radioligands for both SPECT and PET studies.

Serotonin (5-HT) is an essential neurotransmitter for the normal function of the central nervous system. This neurotransmission system in the brain controls various important behaviors, including sleep awake cycle, mood, temperature, appetite, etc. In addition, several commonly used anti-anxienty anxiety drugs (Frazer, A. and J. G. Hensler, *Ann. NY Acad. Sci.* 600:460–475 (1990); Gozlan, H. and M. Hamon, *Anxiety: Neurobiol., Clinic and Ther. Persp.* 232: 141–150 (1993)) and antidepressants (Frazer, A., *J. Clin. Psychiatry* 6:9–25 (1997); Coryell, W., *J Clin. Psychiatry* 1:22–27 (1998); Heninger, G. R. et al., *Pharmacopsychiatry* 29(1):2–11 (1996); Fuller, R. W., *Prog. Drug Res.* 45:167–204 (1995)) interact specifically with serotonin neurotransmission. Pharmacological actions of the antidepressants (selective serotonin reuptake inhibitors; SSRI), such as fluoxetine (Wong, D. T. and F. P. Byrnaster, *Biology* 363: 77–95 (1995)), paroxetine (Holliday, S. M. and G. L. Plosker, *Drugs Aging* 3(3)278–299 (1993)) and sertraline (Lasne, M. C. et al., *Int. J. Rad. Appl. Inst.—Part A, Applied Rad Isot.* 40(2):147–151 (1989)), are based on blockade of presynaptic transporters for serotonin. Thus, studies of radioligand binding to serotonin transporter (SERT) may provide valuable information of these sites in normal and various disease states. Several tritiated ligands including imipramine (Raisman, R. et al., *Eur. J. Pharmacol.* 54:307–308 (1979)), citalopram (D'Amato, R. et al., *Pharmacol. Exp. Ther.* 242(1):364–371 (1987)), paroxetine (Habert, E., et al., *Eur. J. Pharmacol.* 118(1–2):107–114 (1985)) and 6-nitroquipazine (Hashimoto, K., and T. Goromaru, *Biochem. Pharmacol.* 41(11):1679–1682 (1991); Hashimoto K, and T. Goromaru, *Neuropharmacology* 30(2):113–117 (1991)) have been used for in vitro and in vivo studies. A reduced level of SERT labeled by these tritiated ligands has been demonstrated in post mortem brain sections of patients with depression (Perry, E. K. et al., *Br. J. Psychiat.* 142: 188–192 (1983)), Alzheimer's and Parkinson's diseases (D'Amato, R. et al., *Pharmacol Exp. Ther.* 242(1):364–371 (1987)) as well as in the frontal cortex of a suicide victim (Mann, J. J., *Nature Medicine* 4(1):25–30 (1998)). The in vitro binding studies suggest that using in vivo imaging methods to evaluate the density of SERT may be clinically important.

Anti-depressive drugs, such as Prozac, operate to inhibit serotonin reuptake by binding with the serotonin transporter (SERT) protein, effectively blocking the binding of the protein with serotonin. Although Prozac has been found to be an effective anti-depressant treatment, it has side effects which can be serious. Prozac is known to bind to the serotonin transporter (SERT) protein, but the responses of patients can differ widely. Some patients experience greater binding than others. If a patient is not responding to Prozac treatment, there is currently no way to determine why that is the case. Frequently, the physician will simply administer greater doses of the drug, a practice which will not necessarily lead to better results and which can enhance undesirable side effects.

Development of selective tracers for positron emission tomography (PET) and single photon emission tomography (SPECT) have made it possible to study in vivo neuroreceptors or site-specific bindings non-invasively in the human brain. However, development of PET or SPECT tracers specifically for in vivo imaging of SERT has only met with limited success. The most promising radioligand described to date is [$^{11}$C](+)McN5652 for PET imaging (Szabo, Z. et al., *Synapse* 20(1):37–43 (1995); Szabo, Z. et al., *J. Nucl. Med.* 37(5):125 (1996); Szabo, Z. *Behav. Brain Res.* 73(1): 221–224 (1995); Szabo, Z. et al., *J. Cerebral Blood Flow & Metabol.* 15(5):798–805 (1995); Suehiro, M. et al., *J. Nucl. Med.* 34(1):120–127 (1993); Suehiro, M. et al., *Nucl. Med. Biol.* 22(4):543–545 (1995)). Specific binding of [$^{11}$C](+) McN5652 correlates well with the known density of SERT sites in the human brain (Szabo, Z. et al., *Synapse* 20(1): 37–43 (1995)).

Fluorine-18 has some advantages over carbon-11: 1). It has lower positron energy than carbon-11 (0.63 5 vs 0.96 MeV); 2). Because of the long half-life of fluorine18, the PET studies can be performed for more than 2 hours if necessary; 3). The long half-life is convenient for radiosynthesis; and 4). The radioligands can be transported off site when a cyclotron is not available.

Several radioligands have been developed for PET studies of SERT. These include fluorine-18 labeled paroxetine (Suehiro et al., 1991), fluoxetine (Das and Mukherjee, 1993; Hammadi and Crouzel, 1993) and carbon-11 labeled cyanoimipramine (Hashimoto et al., 1987), citalopram (Hume et al., 1992), sertraline (Hume et al., 1989) and fluoxetine (Kilboum et al., 1989; Schaffel et al., 1990; Shiue et al., 1995). All of these radioligands were found not to be the ideal agents for PET studies of SERT due to their low specific-to-nonspecific binding ratios in vivo. For the last decade, [$^{11}$C](+)McN 5652 (FIG. 1) has been the most promising PET agent for studying SERT in humans (Suehiro et al., 1993$_{a,b}$). However, this agent has high nonspecific binding and has only moderate signal contrast in human PET studies (Szabo et al., 1995$_{a,b}$; Buck et al., 2000; Parsey et al., 2000). Additionally, its pharmacokinetics is not optimal due to the short half-life of carbon-11. Labeling (+)McNeil 5652 with fluorine-18 did not improve its imaging properties (Suehiro et al., 1996; Zessin et al., 2001).

SUMMARY OF THE INVENTION

The present invention provides novel compounds of Formula I.

The present invention also provides diagnostic compositions comprising a compound of Formula I and a pharmaceutically acceptable carrier or diluent.

The invention further provides a method of imaging Serotonin Transporters (SERTS) comprising introducing into a patient a detectable quantity of a labeled compound of Formula I or a pharmaceutically acceptable salt, ester, amide or prodrug thereof.

DETAILED DESCRIPTION OF THE INVENTION

Figure 1:
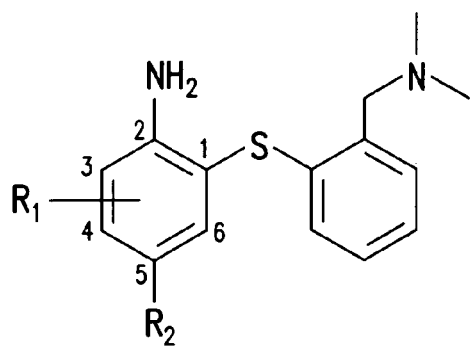
FIG. 1 depicts several compounds of the present invention.
Figure 1:
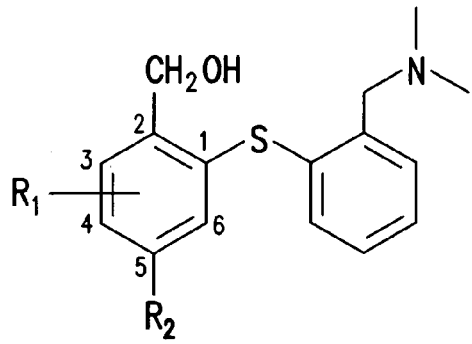
Figure 1:
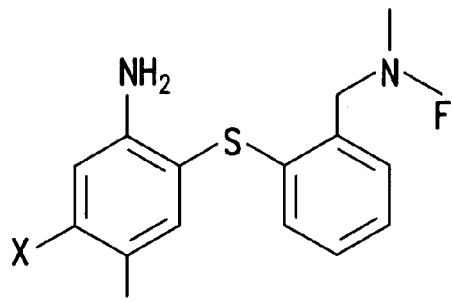

A first aspect of the invention is directed to compounds of Formula I:

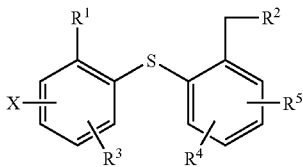

or a pharmaceutically acceptable salt thereof, wherein:
$R^1$ is selected from the group consisting of hydroxy($C_{1-4}$) alkyl, halo($C_{1-4}$)alkyl, nitro, azido, halo or —NR$^6$R$^7$ wherein,
$R^6$ and $R^7$ are each independently selected from the group consisting of hydrogen, $C_{1-4}$ alkyl, halo($C_{1-4}$) alkyl, halo($C_{1-4}$)alkanoyl, and halobenzoyl,
$R^2$ is —NR$^8$R$^9$ wherein,
$R^8$ and $R^9$ are each independently selected from the group consisting of hydrogen, $C_{1-4}$ alkyl, halo($C_{1-4}$) alkyl, halo($C_{1-4}$)alkanoyl, halo benzoyl and,
$R^3$, $R^4$ and $R^5$ are each independently selected from the group consisting of hydrogen, halo, cyano, $C_{1-4}$ alkyl, halo($C_{1-4}$)alkyl, halo($C_{1-4}$)alkanoyl, ($C_{1-4}$)alkoxy, and
X is hydrogen or halo, provided that:
one of $R^1$, $R^2$, $R^3$, $R^4$, $R^5$ or X contains $^{18}$F, and
if $R^1$ is —NR$^6$R$^7$ wherein R$^6$ and R$^7$ are both hydrogen, and
$R^2$ is —NR$^8$R$^9$ wherein R$^8$ and R$^9$ are both methyl, then $R^3$ is hydrogen, halo, cyano, $C_{1-4}$ alkyl, halomethyl or ($C_{1-4}$)alkoxy, and
if $R^1$ is fluoromethyl, then
$R^3$ and X is other than 4-iodine.

Useful values of $R^1$ include hydroxy($C_{1-4}$)alkyl, halo($C_{1-4}$)alkyl, nitro, azido, halo or —NR$^6$R$^7$ wherein, R$^6$ and R$^7$ are each independently selected from the group consisting of hydrogen, $C_{1-4}$ alkyl, halo($C_{1-4}$)alkyl, halo($C_{1-4}$)alkanoyl and halobenzoyl. Preferably, R$^1$ is hydroxy($C_{1-4}$)alkyl or —NR$^6$R$^7$.

When $R^1$ is hydroxy($C_{1-4}$)alkyl, a more preferable value is hydroxymethyl. In such embodiments, useful values of R$^8$ and R$^9$ are independently hydrogen, $C_{1-4}$ alkyl, halo($C_{1-4}$) alkyl, halo($C_{1-4}$)alkanoyl or halobenzoyl. Preferably, one of R$^8$ and R$^9$ is methyl, the other of R$^8$ and R$^9$ is halo($C_{1-4}$)alkyl. In this embodiment, useful values of R$^3$, R$^4$ and R$^5$ are independently hydrogen, halo, cyano, $C_{1-4}$ alkyl, halo($C_{1-4}$) alkyl, halo($C_{1-4}$)alkanoyl or ($C_{1-4}$)alkoxy. Preferably, R$^3$, R$^4$ and R$^5$ are hydrogen. In this embodiment, useful values of X include hydrogen, or halo. In all embodiments, the compound contains $^{18}$F.

When $R^1$ is hydroxymethyl, it is also useful for R$^8$ and R$^9$ to be each independently $C_{1-4}$ alkyl. Preferably, R$^8$ and R$^9$ are each methyl. In this embodiment, useful values of R$^3$, R$^4$ and R$^5$ are independently hydrogen, halo, cyano, $C_{1-4}$ alkyl, halo($C_{1-4}$)alkyl, halo($C_{1-4}$)alkanoyl or ($C_{1-4}$)alkoxy. Preferably, R$^3$ is hydrogen, $C_{1-4}$ alkyl, halo($C_{1-4}$)alkyl, halo($C_{1-4}$) alkanoyl. Preferably, R$^4$ and R$^5$ are each hydrogen. In all embodiments, the compound contains $^{18}$F.

Another useful value of $R^1$ is halo. In this embodiment, it is preferable that R$^8$ and R$^9$ are each $C_{1-4}$ alkyl. In this embodiment, useful values of R$^3$, R$^4$ and R$^5$ are independently hydrogen, halo, cyano, $C_{1-4}$ alkyl, halo($C_{1-4}$)alkyl, halo($C_{1-4}$)alkanoyl or ($C_{1-4}$)alkoxy. Preferably, R$^3$, R$^4$ and R$^5$ are each hydrogen. Preferably, X is halo. In all embodiments, the compound contains $^{18}$F.

In a preferred embodiment, $R^1$ is —NR$^6$R$^7$ wherein, R$^6$ and R$^7$ are each independently selected from the group consisting of hydrogen, $C_{1-4}$ alkyl, halo($C_{1-4}$)alkyl, halo($C_{1-4}$)alkanoyl and halobenzoyl. Preferably, R$^6$ and R$^7$ are each independently selected from the group consisting of $C_{1-4}$ alkyl, halo($C_{1-4}$)alkyl, halo($C_{1-4}$)alkanoyl and halobenzoyl. In this embodiment, preferred compounds include those compounds where R$^8$ and R$^9$ are each $C_{1-4}$alkyl. More preferably, where R$^8$ and R$^9$ are each methyl. In this embodiment, useful values of R$^3$, R$^4$ and R$^5$ are independently hydrogen, halo, cyano, $C_{1-4}$ alkyl, halo($C_{1-4}$)alkyl, halo($C_{1-4}$)alkanoyl or ($C_{1-4}$)alkoxy. Preferably, R$^3$ is cyano or halo, and R$^4$ and R$^5$ are each hydrogen. Preferably, X is hydrogen or halo. In another preferred embodiment, R$^3$ is 4-chloro, and X is 5-F, where R$^4$ and R$^5$ are each hydrogen. In yet another preferred embodiment, R$^3$ and X are each hydrogen, R$^4$ is cyano and R$^5$ is fluoro. In any embodiment, if R$^6$ and R$^7$ are each hydrogen, then R$^3$ and X are either both hydrogen, or R$^3$ is cyano, chloro, bromo or iodo, and X is hydrogen or fluorine. In all embodiments, the compound contains $^{18}$F.

Other useful compounds include compounds where $R^1$ is —NR$^6$R$^7$ wherein, R$^6$ and R$^7$ are each hydrogen, and one of R$^8$ and R$^9$ is hydrogen or $C_{1-4}$ alkyl, the other of R$^8$ and R$^9$ is $C_{1-4}$ alkyl, or halo($C_{1-4}$)alkyl. Preferably, one of R$^8$ and R$^9$ is $C_{1-4}$ alkyl, the other of R$^8$ and R$^9$ is $C_{1-4}$ alkyl or halo($C_{1-4}$)alkyl. Preferably, one of R$^8$ and R$^9$ is halomethyl the other of R$^8$ and R$^9$ is methyl. It is also a preferred embodiment for both R$^8$ and R$^9$ to be methyl. In this embodiment, useful values of R$^3$ include hydrogen, cyano or halomethyl. Preferably, R$^4$ and R$^5$ are each hydrogen. Useful compounds include those where X is hydrogen or halo. More preferably, R$^3$ is hydrogen and X is fluoro. In any embodiment, R$^8$ and R$^9$ are each $C_{1-4}$ alkyl, then R$^3$ is other than cyano. In all embodiments, the compound contains $^{18}$F.

Another aspect of the present invention is directed to a pharmaceutical composition comprising a compound of the present invention, and a pharmaceutically acceptable excipient or diluent.

In another aspect, the present invention is directed to a diagnostic composition for imaging serotonin transporters, comprising a compound of the present invention, and a pharmaceutically acceptable excipient or diluent.

In yet another aspect, the present invention is directed to a method of imaging serotonin transporters in a mammal, comprising administering a detectable quantity of a diagnostic composition of the present invention.

When any variable occurs more than one time in any constituent or in Formula I its definition on each occurrence is independent of its definition at every other occurrence. Also combinations of substituents and/or variables are permissible only if such combinations result in stable compounds.

The term "alkyl" as employed herein by itself or as part of another group refers to both straight and branched chain radicals of up to 8 carbons, preferably 6 carbons, more preferably 4 carbons, such as methyl, ethyl, propyl, isopropyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1–4 carbon atoms in length.

The term "halo" employed herein by itself or as part of another group refers to chlorine, bromine, fluorine or iodine.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

The term "hydroxyalkyl" as employed herein refers to a group containing a hydroxyl group attached to a carbon chain, wherein said alkyl chain is attached to Formula I or a substituent of Formula I as described above.

The term "haloalkanoyl" as employed herein refers to a group containing an alkyl chain to which a halo is attached at one terminus, and the other terminus is attached to a carbonyl, wherein the alkanoyl is attached to Formula I or a substituent of Formula I through said carbonyl.

The term "benzoalkanoyl" as employed herein refers to a group containing a benzyl moiety to which a carbonyl is attached, wherein the benzoalkanoyl is attached to Formula I or a substituent of Formula I through said carbonyl.

N,N-dimethyl-2-(2-nitro-4-bromophenylthio)benzylamine (4) and N,N-dimethyl-2-(2,4-dinitrophenylthio)benzylamine (8) were prepared in multi-steps synthesis as precursors for the synthesis of a new serotonin transporter imaging agent. N,N-dimethyl-2-(2-amino-4-[$^{18}$F]fluorophenylthio)benzylamine (12a). The bromo precursor, N,N-dimethyl-2-(2-nitro-4-bromophenylthio)benzylamine (4) was prepared by the reaction of 2,5-dibromonitrobenzene (1) with 2-thio-N,N-dimethylbenzamide followed by reduction with $BH_3$. Reaction of compound 1 with 2-thio-N,N-dimethylberizamide gave N,N-dimethyl-2-(2-nitro-4-bromophenylthio)-benzamide (3) as the major product. Reduction of compound 3 with $BH_3$ gave N,N-dimethyl-2-(2-nitro-4-bromophenylthio)benzylamine (4) along with its amine borane (5), respectively in a ratio of 5 to 1 (Scheme 1). The formation of compound 5 from this reaction was somewhat unexpected as it was not reported in the literature from the same reaction (Oya et al., 1999). However, the formation of N,N-dimethyl-2-(3-methoxyphenylthio)benzamine borane from the reduction of N,N-dimethyl-2-(3-methoxyphenylthio)benzamide with $BH_3$ was reported previously (Jilek et al., 1989).

The other precursor, N,N-dimethyl-2-(2,4-dinitrophenylthio)benzylamine (8) was synthesized similarly in two steps. Reaction of 2-bromo-1,5-dinitrobenzene (2) with 2-thio-N,N-dimethylbenzamide gave N,N-dimethyl-2-(2,4-dinitrophenylthio)benzamide (6). In contrast to compound 3, reduction of compound 6 with $BH_3$ gave N,N-dimethyl-2-(2,4-dinitrophenylthio)benzylamine.$BH_3$ (7) as the major product (54%) (Scheme 1). Compound 7 was converted to its free base (8) by refluxing it in 0.5 N HCl for 2 hrs followed by purification.

The authentic sample, N,N-dimethyl-2-(2-amino-4-fluorophenylthio)benzylamine (12) vas also synthesized in multisteps. Reaction of 2-chloro-5-fluoronitrobenzene with 2-thio-N,N-dimethylbenzamide gave N,N-dimethyl-2-(2-nitro-4-fluorophenylthio)-benzamide (9). Reduction of compound 9 with $BH_3$ gave N,N-dimethyl-2-(2-nitro-4-fluorophenylthio)benzylamine (10) and its amine borane (11) in a ratio of ~1:1 (Scheme 1). Compound 10 was reduced further with $SnCl2$ to give the final product (12).

The reduction of nitro group to amino group poses a challenge to this study. While $SnCl_2$, is a good agent for reducing nitro group to amino group in the "cold" chemlstry, it is not an ideal reducing agent for the "hot" chemistry due to the time constraints of fluorine-18. Rather, we have found that $NaBH4-Cu(OAC)_2$ is an ideal agent for the reduction of the nitro group to amino group in the "hot" chemistry. The identities of all the products were verified by elemental analysis and NMR. The chemical shifts (δ) of the methylene group and the methyl group in N,N-dimethylbenzylamines (4, 8, 10)are distinctly different from their amine boranes (5, 7, 11). The chemical shifts (δ) of the methylene group and the methyl group in N,N-dimethylbenzylamines are 3.5 and 2.2 respectively, while they are 4.2 and 2.6, respectively, in their amine boranes. This is prbably due to the inductive effect of $BH_3$.

The aromatic nucleophilic substitution is an efficient method for the synthesis of no-carrier-added fluorine-18 labeled arenes (Attina et al. 1983$_{a,b}$; Angelini et al. 1984, 1985, Berridge et al. 1985; Shiue et al. 1984; Mishani et al. 1995). In general, a good leaving group in ortho or para position to a strongly electron-withdrawing group is required to facilitate this process. Recently, Constantinon et al (2001) reported that electron-withdrawing m-substituted nitrobenzenes reacted with no-carrier-added [18F]fluoride to give fluorine-18 labeled m-disubstituted benzenes in low to moderate yields. We have adapted this method to synthesize a new fluorine-18 labeled serotonin transporter imaging agent, N,N-dimethyl-2-(2-amino-4-[$^{18}$F]fluorophenylthio)-benzylamine (12a). Reaction of the bromo-(4) or nitro-(8) precursors with K[$^{18}$F]/Kryptox 2.2.2 in DMSO at 130° C. gave N,N-dimethyl-2-(2-nitro-4-[$^{18}$F]fluorophenylthio)benzylamine (10a). Reduction of compound 10a with $SnCl_2$ proceeded slowly. However, compound 10a was reduced to compound 12a with Cu(Oac)—$NaBH_4$ in nearly quantitative yield. The overall radiochemical yield of compound 12a synthesized by this method was ~5–10% in a synthesis time of 150 min from EOB. The radiochemical purity of compound 12a was >98%. The radiochemical yield of compound 12a was not optimized.

A preliminary biodistribution study in rats showed that the uptake of compound 12a in rat brain was high (~1%/g) and the ratio of the uptake of compound 12a in serotonin transporter-rich area (hypothalamus) to serotonin transporter-devoid area (cerebellum) was 6/1 at 1 hr. post-injection, suggesting compound 12a may be a potential new serotorim transporter imaging agent using PET.

Schemes 1–5 depict synthetic routes for amino-[18]fluorophenylthiobenzylamine derivatives of the present invention.

We have labeled N,N-dimethyl-2-(2-amino-4fluorophenylthio)benzylamine (12) with fluorine-18 by nucleophilic substitution of the corresponding precursors, namely N,N-dimethyl-2-(2-nitro-4-bromophenylthio)benzylamine (4) and N,N-dimethyl-2-(2,4-dinitrophenylthio)benzylamine (8) with K[$^{18}$F] followed by reduction with NaBH$_4$—Cu(OAC)$_2$ in 5–10% yield in a synthesis time of 150 minutes from EOB.

Precursors 4 and 8 were prepared in multi-steps synthesis. Reaction of 2,5dibromonitrobenzene (1) with 2-thio-N,N-dimethylbenzamide gave N N-dimethyl-2-(2-nitro-4-bromophenylthio)benzamide (3). N,N-Dimethyl-2-(2,4-dinitrophenylthio)-benzamide (6) was synthesized similarly from the reaction of 2-bromo-1,5-dinitro-benzene (2) with 2-thio-N,N-dimethylbenzamide. Reduction of 3 and 6 with BH$_3$/THF gave benzylamines (4) and (8) along with their amine boranes (5) and (7) (Scheme 1). Nucleophilic substitution of (4) or (8) with K[$^{18}$F]/Kryptofix 2.2.2 in DMSO at 120° C. followed by reduction with NaBH$_4$—Cu(OAC)$_2$ in EtOH at 78° C. and purification with HPLC gave 4-[$^{18}$F]-ADAM (12a) in ~5–10% yield in a synthesis time of 150 min from EOB.

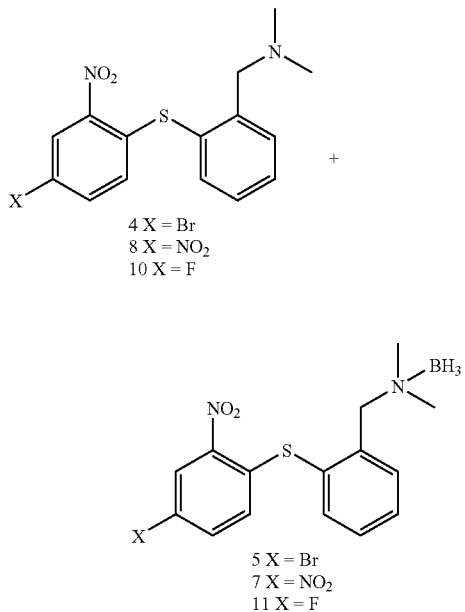

SCHEME 1.

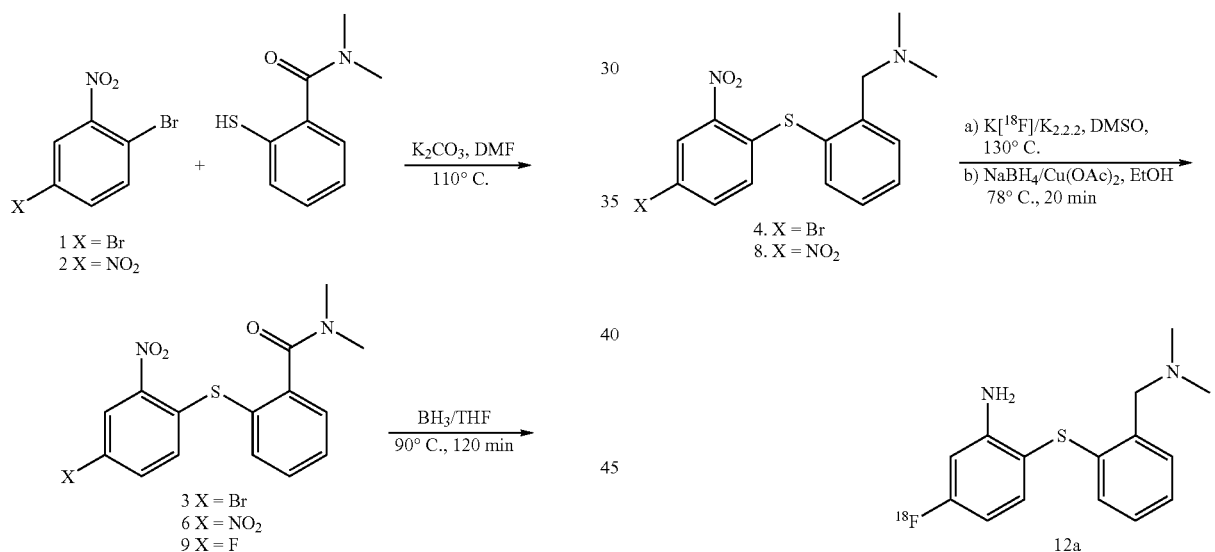

SCHEME 2.

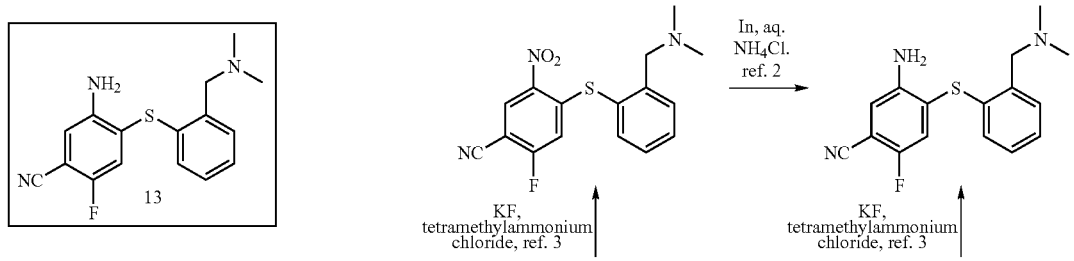

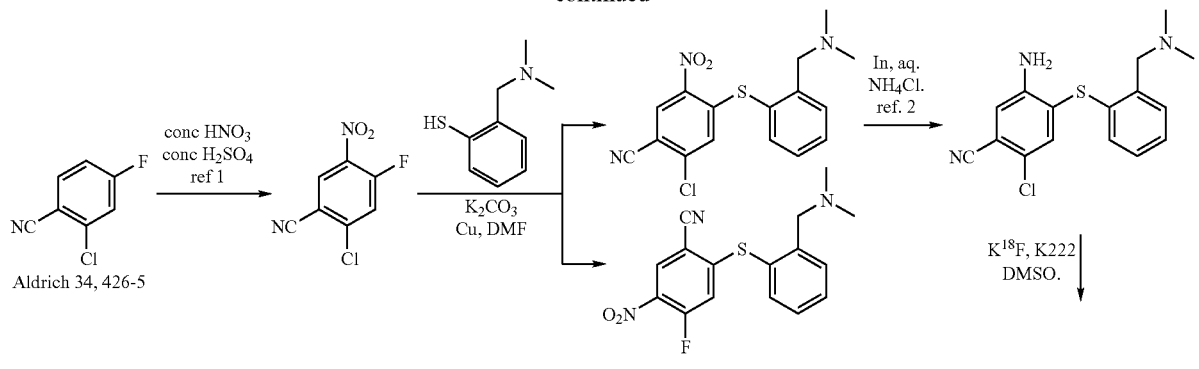
ref. 1 Kudo et al; Chem. Pharm. Bull.; 44; 9; 1996; 1663-1668
ref. 2 Moody et al; Syn. Lett.; 9; 1998; 1028
ref. 3 Sasson et al; J.C.S. Chem. Commun.; 3; 1996; 297-298
SCHEME 3
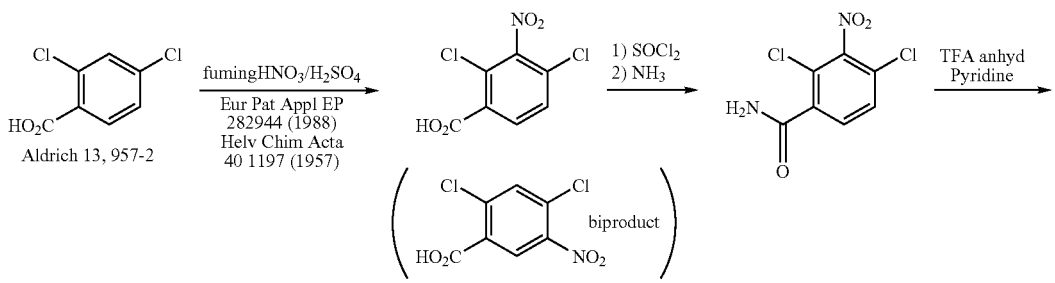
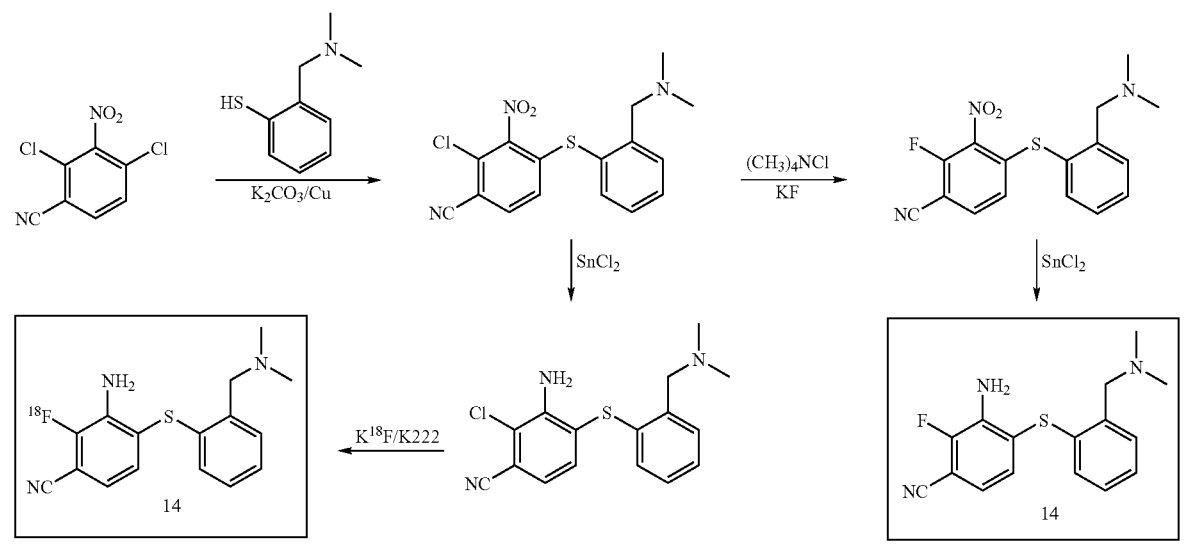

SCHEME 4
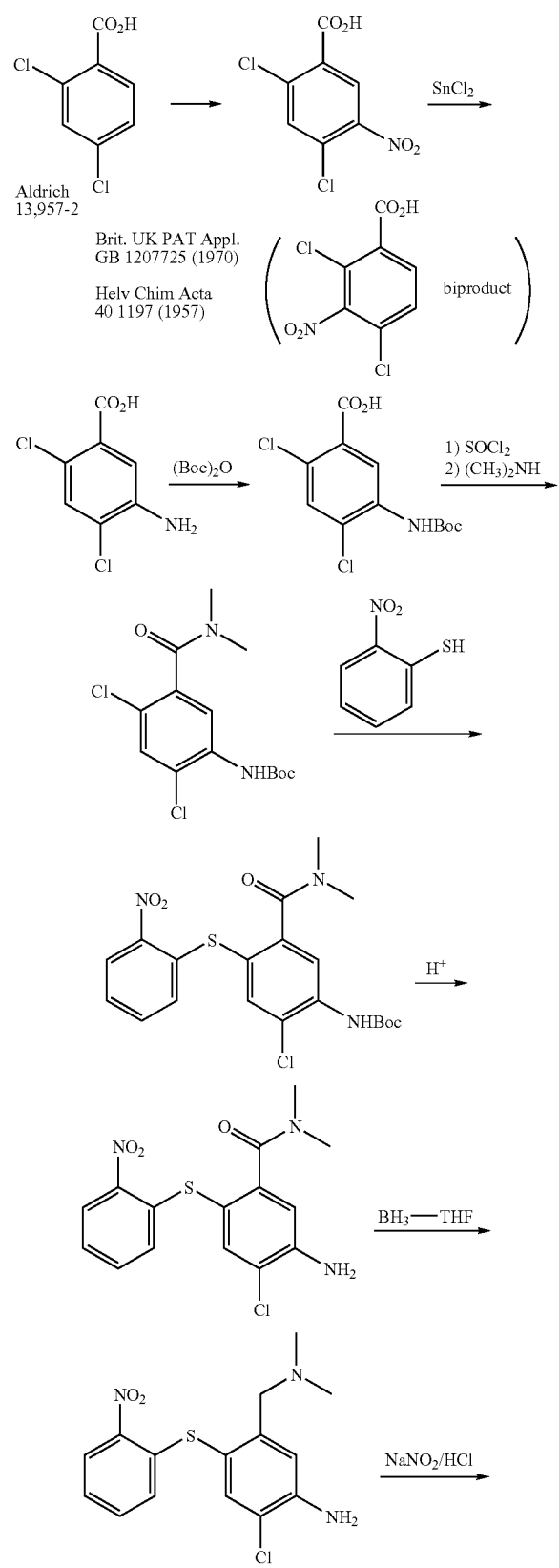
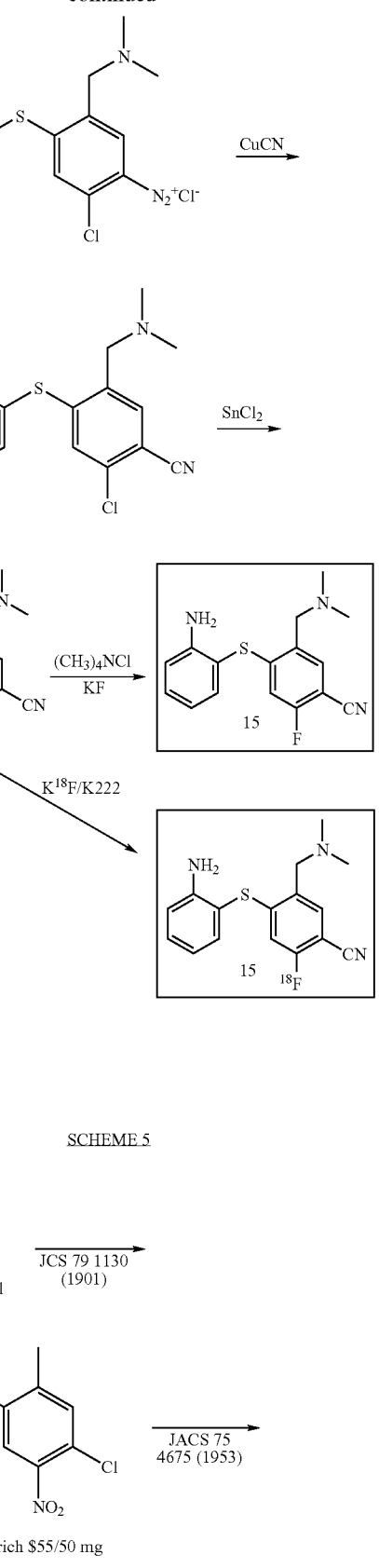
SCHEME 5

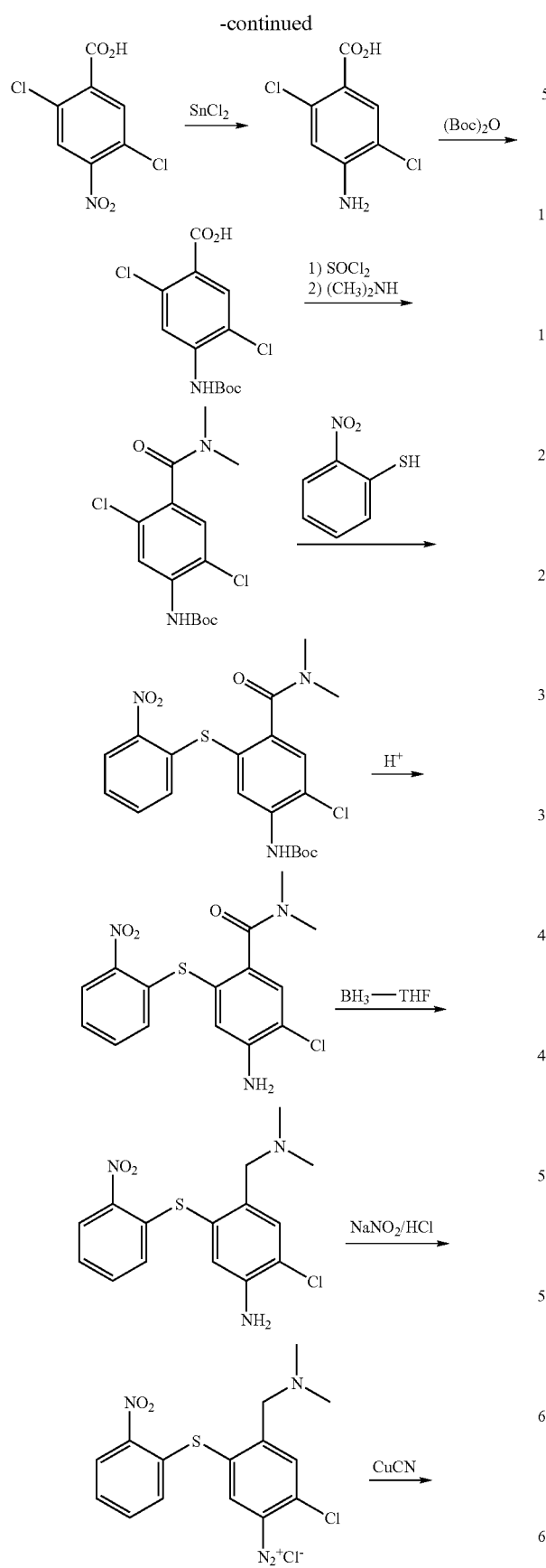
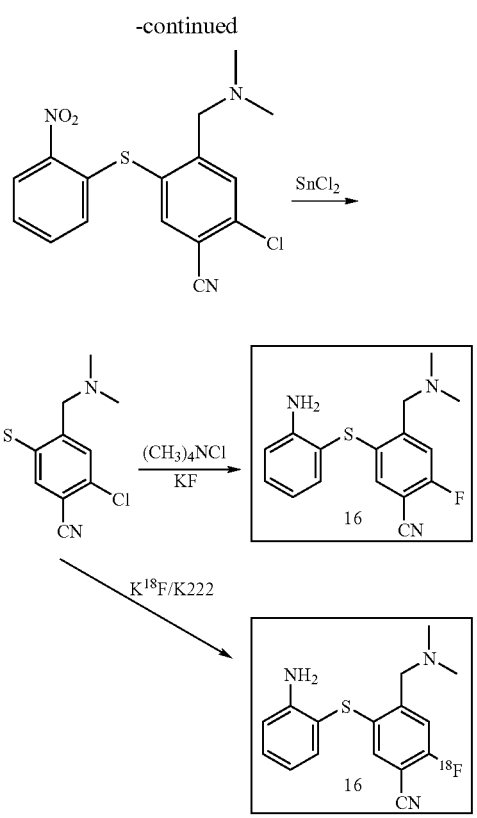
SCHEME 6
Synthesis of non-radioactive ACF 25
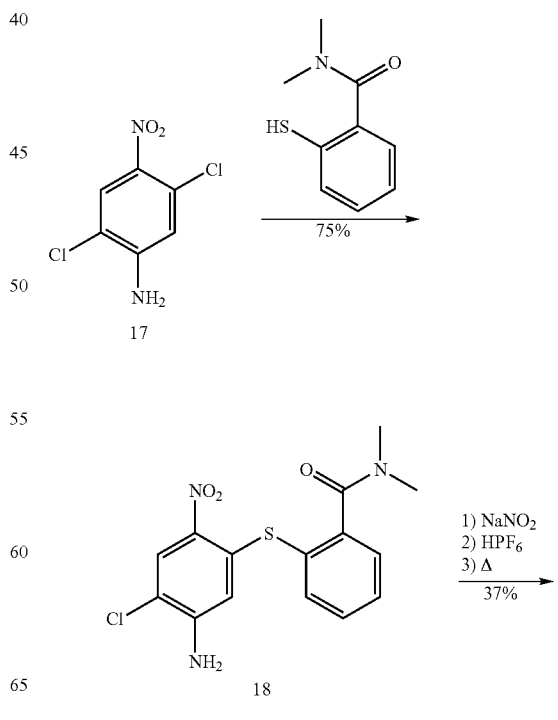

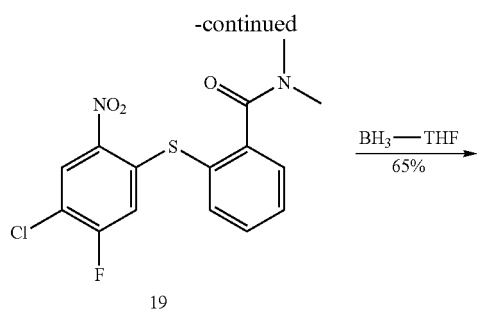

19

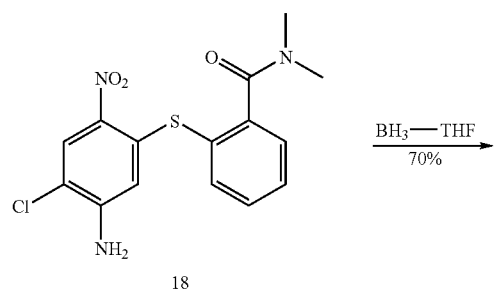

18

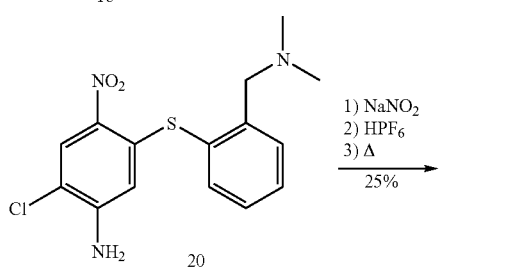

20

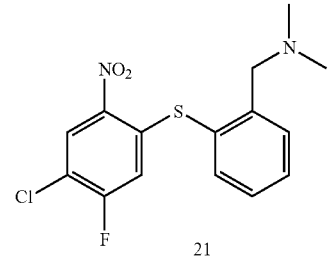

21

Synthesis of precursor 23

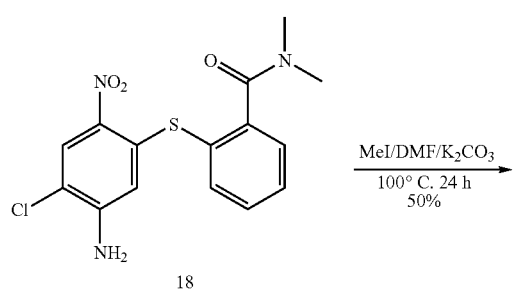

18

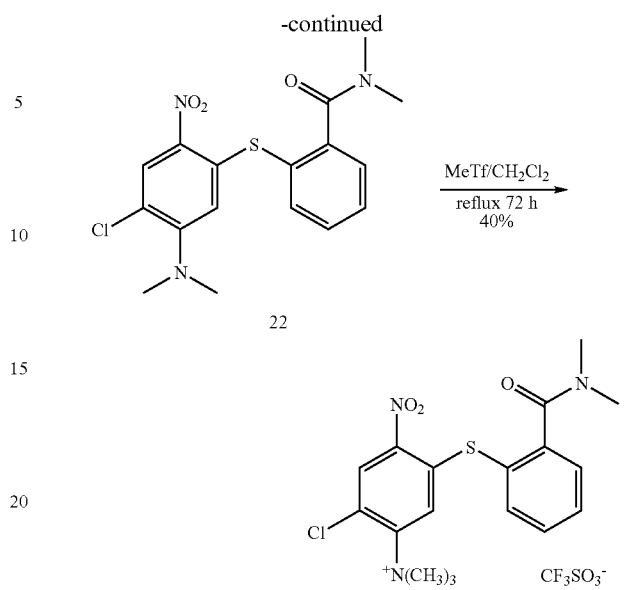

22

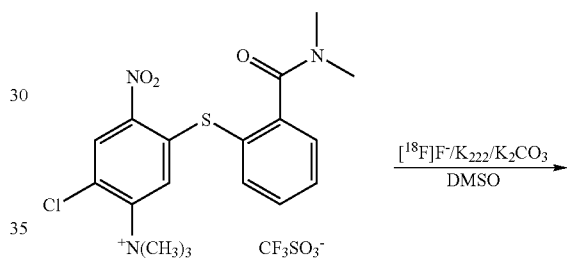

23

Synthesis of F-18 labeled ACF ([$^{18}$F] 25

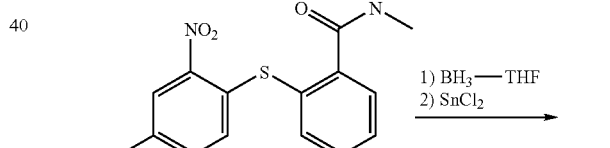

23

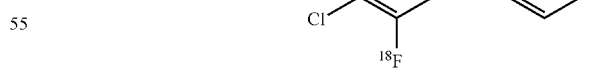

24

[$^{18}$F] 25

Recently, a new class of potent serotonin reuptake inhibitors, namely the N,N-dimethyl-2-(arylthio)benzylamines, have been reported to possess very high selectivity and affinity for SERT over norepinephrine transporter and dopamine transporter binding sites (Jilek et al., 1989; Ferris et al., 1995). Analogs have been labeled with iodine-123 (IDAM, ADAM and ODAM) (Oya et al., 1999, 2000; Kung et al., 1999; Acton et al., 1999$_{a,b}$, 2001) and carbon-11 ([$^{11}$C]IDAM, [$^{11}$C]ADAM, [$^{11}$C]DAPP, [$^{11}$C]DASB, [$^{11}$C] AFM and [$^{11}$C]BrADAM (Shiue et al., 2000; Wilson et al., 1999,2000; Huang, 2001a,b; Jarkas et al., 2001; Vercouillie et al., 2001) as SERT SPECT and PET agents. ["C]DASB, in particular, has been found to be highly suitable for probing the serotonin reuptake system with PET in humans (Houle et al., 2000; Ginovart et al., 2001).

One of the fluorine-18 labeled compounds, N,N-dimethyl2-(2-fluoromethyl-4-iodophenylthio)benzylamine (F-IDAM) had high affinity toward SERT ($K_i$=0.003 nM) and showed excellent initial brain uptake and binding properties in rats (Oya et al., 2001). This compound, however, defluorinated rapidly in baboon and was not the ligand of choice for PET studies of SERT in baboon or humans. Other fluorinated analogs of IDAM and ADAM also showed high affinity toward SERT (Huang et al., 2001b; Jarkas et al., 2001). Two of these compounds, NN-[$^{11}$C]dimethyl2-(2-amino-4-fluorophenylthio)benzylamine (12, 4-F-ADAM) and N,N-[$^{11}$C]dimethyl-2-(2-amino-4-fluoromethylphenylthio)benzylamine (AFM) had high affinity and selectivity toward SERT ($K_i$=4.8 and 1.8 nM, respectively) and showed excellent brain uptake and a high degree of specific binding in rats (Huang et al., 2001b). However, as discussed above, fluorine-18 labeled radioligands have certain advantages compared to carbon-11 labeled compounds, therefore, In vitro binding assays showed that 4-F-ADAM displayed high affinity to SERT sites (Ki=0.081 nM, using membrane preparations of LLC-PKI cells expressing the specific transporter) and showed more than 1000- and 28000-fold of selectivity for SERT over NET and DAT, respectively. Biodistribution of 4-[$^{18}$F]-ADAM in rats showed a high initial uptake and slow clearance in the brain (2.13, 1.90 and 0.95% dose/organ at 2, 30 and 60 min after i.v. injection, respectively) with the specific binding peaked at 2 h post-injection (hypothalamus-cerebellum/cerebellum=12.49). The initial uptake in blood, muscle, lung, kidney and liver were also high, but it cleared rapidly. The radioactivity in the femur increases with time for 4-[$^{18}$F]-ADAM indicating that in vivo defluorination may occur in rats. In vivo metabolism study in rats showed that 4-[$^{18}$F]ADAM was not metabolized in rat brain (>96% of radioactivity was recovered as parent compound). However, it metabolized rapidly in the blood. Only <7% of radioactivity recovered from plasma was the parent compound and the majority of radioactivity in plasma was not extractable by ethyl acetate. Blocking studies showed that there were significant decreases on the uptake of 4-[$^{18}$F]-ADAM in the brain regions (hypothalamus, hippocampus and striatum) where SERT concentrations are high when rats were pretreated with (+)McN 5652 (2 mg/kg 5 min prior to IV injection of 4-[$^{18}$F]-ADAM). However, there were no significant changes on the uptake of 4-[$^{18}$F]-ADAM in these brain regions when rats were pretreated with either methylphenidate or nisoxetine. Baboon study showed that the uptake of 4-[$^{18}$F]-ADAM in the midbrain peaked at ~1 h post-injection and then declines slowly. The ratio of radioactivity in midbrain to that in cerebellum (where it had low concentration of SERT) was ~3.5–4 at 2 h post-injection of 4-[$^{18}$F]-ADAM. The uptake in the skull did not increase with time indicating that in vivo defluorination may not occur in baboon. These results suggest that 4-["F]-ADAM is suitable as a PET ligand for studying SERT in living brain.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

Reagents and solvents were purchased from Aldrich and used without further purification. $C_{18}$ Sep-Pak cartridges were obtained from Waters Chromatography Division, Millipore Corporation. Radioactivity was determined using a calibrated ion chamber (Capintec CRC-745, Capintec, Inc.) and a sodium iodide well counter (Packard, Gamma Counter 5000 Series, Packard Instrument Company, IL).

High performance liquid chromatography (HPLC) analyses were carried out with a Sonntek liquid chromatograph equipped with both u.v. and radioactivity monitors. For the semi-preparative separations, a reversed phase $C_{18}$ column (10×250 mm, Phenomenex Luna (2)) was used with $CH_3CN$:0.1 M $HCO_2NH_4$ (30:70) containing 0.3 v % of acetic acid as the solvent with a flow rate of 5 ml/min. For the specific activity determinations, an analytical reversed phase $C_{18}$ column (4.6×250 mm, Phenomenex Luna (2)) was used with the same solvent as that used for the semi-preparative separations with a flow rate of 0.8 ml/min.

The elemental analyses were performed by Atlantic Microlab, Inc. Norcross, Ga. Elemental compositions were within ±0.3% of the calculated values. Melting points were determined on a MEL-Temp II apparatus and are uncorrected. $^1H$ NMR spectra were recorded on a Bruker DPX 200 spectrometer. Chemical shifts (δ) are expressed in parts per million relative to internal tetramethylsilane. Single-Crystal X-ray Crystallography of compounds 4 ($C_{15}H_{15}SN_2O_2Br$) and 5 ($C_{15}H_{18}BSN_2O_2Br$) were performed by X-Ray Diffraction Laboratory, Chemistry Department, University of Pennsylvania.

Example 1

N,N-Dimethyl-2-(2-nitro-4-bromophenylthio)benzamide (3)

A mixture of 2,5-dibromonitrobenzene (1; 1.71 g, 61 mmol), 2-thio-N,N-dimethylbenzamide (1.18 g, 68 mmol) which was fresh prepared before use by the reported procedure (Douglass and Farah, 1961; Okachi et al., 1985) and potassium carbonate (3 g) in dimethylformamide (20 mL) was heated at 90–110° C. for 24 h. After cooling down to room temperature, the reaction mixture was poured into cold water (200 mL). The precipitates were collected and recyrstallized from ethanol to give compound 3 as a yellow solid (1.64 g, 70%): mp 112.5–114° C.; $^1H$ NMR ($CDCl_3$) δ 8.32 (d, J=2.2 Hz, 1H), 7.41–7.62 (m, 5H), 6.80 (d, J=8.7 Hz, 1H), 3.04 (s, 3H), 2.85 (s, 3H). Anal. Calcd for $C_{15}H_{13}BrN_2O_3S$: C, 47.26; H, 3.44; N, 7.35. Found: C, 47.30; H, 3.56; N, 7.30.

Example 2

N,N-Dimethyl-2-(2-nitro-4-bromophenylthio)benzylamine (4) and N,N-Dimethyl-2-(2-nitro-4-bromophenylthio)benzylamine.$BH_3$ (5)

To the solution of compound 3 (0.653 g, 1.71 mmol) in anhydrous THF (10 mL), $BH_3$-THF complex (1 M solution, 5 mL) was added at 0° C. The mixture was refluxed for 2 hrs, cooled to 0° C., acidified with HCl (1 N) and the solvent was evaporated to dryness. Water (20 mL) was added to the residue and the mixture was refluxed for 30 min. After cooling down to room temperature, the mixture was adjusted to pH 8 with saturated $NaHCO_3$ solution and extracted with $CH_2Cl_2$ (30 mL×3). The combined organic layer was dried over $MgSO_4$ and the solvent was removed under reduced pressure. The resulting residue was separated by silica gel column chromatography. The column was first eluted with $CH_2Cl_2$ to give compound 5 (0.10 g, $R_f$=0.95; $CH_2Cl_2$/$CH_3OH$, 90/10), mp 120–122° C.; $^1H$ NMR ($CDCl_3$) δ 8.40 (d, J=2.2 Hz, 1H), 7.78 (d, $J_1$=1.74 Hz, $J_2$=7.6 Hz, 1H), 7.47–7.66 (m, 3H), 7.39–7.44 (q, $J_1$=2.2 Hz, $J_2$=8.7 Hz, 1H), 6.37 (d, J=8.7 Hz, 1H), 4.19 (s, 2H), 2.60 (s, 6H). Anal. Calcd for $C_{15}H_{18}BrN_2O_2BS$: C, 47.75; H, 4.44; N, 7.27. Found: C, 47.37; H, 4.75; N, 7.29. The column was then eluted with $CH_2Cl_2$/$CH_3OH$ to give compound 4 (0.50 g, $R_f$=0.45; $CH_2Cl_2$/$CH_3OH$, 90/10), mp 96–98° C. (oil, Oya et al., 1999); $^1H$ NMR ($CDCl_3$) δ 8.37 (d, J=2.2 Hz, 1H), 7.66 (d, J=7.8 Hz, 1H), 7.46–7.56 (m, 2H), 7.31–7.41 (m, $J_1$=2.2 Hz, $J_2$=8.7 Hz, $J_3$=1.6 Hz, 2H), 6.56 (d, J=8.7 Hz, 1H), 3.52 (s, 2H), 2.18 (s, 6H). Anal. Calcd for $C_{15}H_{15}BrN_2O_2S$: C, 49.06; H, 4.12; N, 7.63). Found: C, 49.27; H, 4.10; N, 7.57.

Example 3

N-N-Dimethyl-2-(2,4-dinitrophenylthio)benzamide (6)

A mixture of 2-bromo-1,5-dinitrobenzene (2; 2.47 g, 10.0 mmol), 2-thio-N,N-dimethylbenzamide (2.00 g, 11.3 mmol) and sodium methoxide (1.30 g) in dimethylformamide (25 mL) was heated at 90–110° C. for 36 h. The reaction mixture was filtered by suction and the solid was discarded. The filtrate was evaporated to dryness, water (25 mL) was added and the solution was extracted with methylene chloride. The combined organic layer was dried over $Na_2SO_4$ and the solvent was evaporated in vacuo to dryness. The residue was purified by silica gel chromatography. The column was first eluted with $CH_2Cl_2$ and the eluate was discarded. The product was eluted with $CH_2Cl_2$/$CH_3OH$ (90/10) and recrystallized from methylene chloride/hexane to afford compound 6 as a yellow solid (2.63 g, 75.7%), mp 147–149° C. $R_f$=0.8 (silica gel, $CH_2Cl_2$/$CH_3OH$, 90/10). $^1HNMR$ ($CDCl_3$) δ 9.07 (d, J=2.4 Hz, 1H), 8.15 (q, $J_1$32 2.4 Hz, $J_2$=9.0 Hz, 1H), 7.33–7.70 (m, 4H), 7.06 (d, J=9.0 Hz, 1H), 3.04 (s, 3H), 2.88 (s, 3H). Anal. Calcd for $C_{15}H_{13}N_3O_5S$: C, 51.87; H, 3.77; N, 12.10. Found: C, 51.69; H, 3.74; N, 12.02.

Example 4

N,N-Dimethyl-2-(2,4-dinitrophenylthio)benzylamine.$BH_3$ (7)

To the solution of compound 6 (1.83 g, 5.27 mmol) in anhydrous THF (20 mL), $BH_3$-THF complex (1 M solution, 20 mL) was added at 0° C. The mixture was refluxed for 2 h, cooled to 0° C., acidified with 1 N HCl and the solvent was removed under reduced pressure. Water (30 mL) was added to the residue. The precipitates were collected, washed with water and recrystallized from methylene chloride/hexane to give compound 7 as a yellow solid (0.98 g, 54%), mp 165–167° C., $R_f$=0.7 (silica gel, $CH_2Cl_2$). $^1H$ NMR ($CDCl_3$) δ 9.14 (d, J=2.5 Hz, 1H), 8.13 (q, $J_1$=2.5 Hz, $J_2$=9.0 Hz, 1H), 7.77–7.85 (m, 1H), 7.54–7.70 (m, 3H), 6.65 (d, J=9.0 Hz, 1H), 4.19 (s, 2H), 2.62 (s, 6H). Anal. Calcd for $C_{15}H_{18}N_3O_4BS$: C, 51.89; H, 5.23; N, 12.10. Found: C, 51.87; H, 5.18; N, 12.08.

Example 5

N,N-Dimethyl-2-(2,4-dinitrophenylthio)benzylamine (8)

A mixture of compound 7 (280 mg, 0.806 mmol) in 10 mL of methanol and 25 mL of 0.5 N HCl was refluxed for 2 hrs. The methanol was removed under reduced pressure and the residue was adjusted to pH 8 with saturated $NaHCO_3$ solution. The solution was extracted with $CH_2Cl_2$ (30 mL×3). The combined organic layer was dried over $Na_2SO_4$ and the solvent was evaporated to dryness. The residue was separated by silica gel chromatography. The column was eluted with $CH_2Cl_2$ first and the eluates was discarded. The column was then eluted with $CH_2Cl_2$/$CH_3OH$ (98/2) to yield compound 8 as a yellow solid (161 mg, 56%), mp 122–124° C.; $R_f$=0.4–0.5 (silica gel, $CH_2Cl$/$CH_3OH$ (9/1)). $^1H$ NMR ($CDCl_3$) δ 9.14 (d, J=2.46 Hz, 1H), 8.08 (q, $J_1$=2.46 Hz, $J_2$=9.0 Hz, 1H), 7.53–7.68 (m, 3H), 7.37–7.45 (m, 1H), 6.83 (d, J=9.0 Hz, 1H), 3.51 (s, 2H), 2.14 (s, 6H). Anal. Calcd for $C_{15}H_{15}N_3O_4S$: C, 54.04; H, 4.54; N, 12.60. Found: C, 53.87; H, 4.56; N, 12.36.

Example 6

N,N-Dimethyl-2-(2-nitro-4-fluorophenylthio)benzamide (9)

A mixture of 2-chloro-5-fluoronitrobenzene (1.94 g, 110 mmol), 2-thio-N,N-dimethylbenzamide (2.4 g, 132 mmol,) and sodium methoxide (1.1 g) in dimethylformamide (20 mL) was heated at 90–110° C. for 36 h. and processed as described above. The residue was purified by silica gel chromatography. The column was eluted with $CH_2Cl_2$, followed by $CH_2Cl_2$/$CH_3OH$ (90/10) to give compounds 9 as a brown oil (2.05 g, 58%). $R_f$=0.8 ($CH_2Cl_2$/$CH_3OH$; 90/10)). $^1H$ NMR ($CDCl_3$) δ 7.89 (q, $J_1$=2.8 Hz, $J_2$=8.4 Hz, 1H), 7.39–7.59 (m, 4H), 7.12 (m, $J_1$=2.8 Hz, $J_2$=8.4 Hz, 1H), 6.95 (q, $J_1$=5.2 Hz, $J_2$=9.0 Hz, 1H), 3.03 (s, 3H), 2.84 (s, 3H). Compound 9 was used for the next step without further purification.

Example 7

N,N-Dimethyl-2-(2-nitro-4-fluorophenylthio)benzylamine (10) and N,N-Dimethyl-2-(2-nitro-4-fluorophenylthio)benzylamine.$BH_3$ (11)

To the solution of compound 9 (1.85 g, 5.78 mmol) in anhydrous THF (15 mL), $BH_3$-THF complex (1 M solution, 15 mL) was added at 0° C. The mixture was refluxed for 2 hrs and processed as described above. The residue was separated by silica gel chromatography. The column was eluted first with $CH_2Cl_2$ to give compound 10 (0.45 g), mp 57–59° C.; $^1H$ NMR ($CDCl_3$) δ 7.95 (q, $J_1$=2.8 Hz, $J_2$=8.4 Hz, 1H), 7.64 (m, 1H), 7.48–7.56 (m, $J_1$=1.5 Hz, $J_2$=7.5 Hz, 2H), 7.30–7.38 (m, $J_1$=1.6 Hz, $J_2$=7.5 Hz, 1H), 7.02–7.12 (m, $J_1$=2.8 Hz, $J_2$=7.2 Hz, $J_3$=9.0 Hz, 1H), 6.70 (q, $J_1$=5.2 Hz, $J_2$=9.0 Hz, 1H), 3.52 (s, 2H), 2.18 (s, 6H). Anal. Calcd for $C_{15}H_{15}FN_2O_2S$: C, 58.81; H, 4.94; N, 9.14. Found: C. 58.72; H, 4.93; N, 9.00. The column was then eluted with $CH_2Cl_2$/$CH_3OH$ (95/5) to give compound 11 (0.47 g), mp 91–93° C.; $^1H$ NMR ($CDC_{l3}$) δ 7.99 (q, $J_1$=2.8 Hz, $J_2$=8.2 Hz, 1H), 7.75 (m, $J_1$32 1.8 Hz, $J_2$=7.1 Hz, 1H), 7.45–7.65 (m, $J_1$=1.8 Hz, $J_2$=2.0 Hz, $J_3$=7.5 Hz, 3H), 7.05–7.15 (m, $J_1$=2.8 Hz, $J_2$=7.1 Hz, $J_3$=9.0 Hz, 1H), 6.52 (q, $J_1$=5.1 Hz, $J_2$=9.0 Hz, 1H), 4.21 (s, 2H), 2.60 (s, 6H). Anal. Calcd for $C_{15}H_{18}FN_2O_2BS$: C, 56.27; H, 5.67; N, 8.75; F, 5.93. Found: C, 56.40; H, 5.68; N, 8.66; F, 5.69. The $R_f$ (silica gel, $CH_2Cl_2/CH_3OH$; 90/10) of compounds 10 and 11 are 0.45 and 0.95, respectively.

Example 8

N,N-Dimethyl-2-(2-amino-4-fluorophenylthio)benzylamine (12)

To a yellow solution of compound 10 (200 mg, 0.65 mmol) in $CH_3OH$ (4 mL) and conc. HCl (2 mL), $SnCl_2$ (0–3 g) was added. The mixture was stirred at room temperature overnight and the solvent was evaporated to dryness. Water (15 mL) was added to the residue and the mixture was extracted with ethyl acetate (10 mL×3). The organic layer was discarded and the aqueous layer was adjusted to pH 10 with 1 N NaOH. The cloudy solution was extracted with ethyl acetate (10 mL×3). The combined organic layer was dried over $Na_2SO_4$ and the solvent was evaporated in vacuo to dryness. The residue was purified by column chromatography (silica gel, $CH_2Cl_2/CH_3OH$, 95/5) to yield compound 12 as a white solid (77 mg, 42.7%), $R_f$=0.3 (silica gel, $CH_2Cl_2/CH_3OH$, 90/10), mp 56–58° C.; $^1H$ NMR ($CDCl_3$) δ 7.40–7.49 (m, 1H), 7.18–7.25 (m, 1H), 7.05–7.13 (m, 2H), 6.84–6.93) (m, 1H), 6.38–6.48 (m, 2H), 4.74 (s, b, 2H), 3.57 (s, 2H), 2.31 (s, 6H). Anal. Calcd for $C_{15}H_{17}FN_2S$: C, 65.19; H, 6.20; N, 10.14. Found: C, 65.06; H, 6.23; N, 10.04.

Example 9

N,N-Dimethyl-2-(2-amino-4-[$^{18}$F]fluorophenylthio) benzylamine (12a)

Compound 12a was synthesized by nucleophilic substitution of the corresponding bromo-(4) or nitro-(8) precursor with potassium [$^{18}$F]fluoride/Kryptofix 2.2.2 followed by reduction with $NaBH_4$—$Cu(OAc)_2$ and HPLC purification. Thus, no-carrier-added (NCA) aqueous [$^{18}$F]fluoride (0.5 mL) prepared by the 180(p,n)$^{18}$F nuclear reaction in a JSW BC 30/15 cyclotron on an enriched water (95+% $^{18}$O) target was added to a Pyrex vessel which contains 1.4 mg of $K_2CO_3$ and 10 mg of Kryptofix 2.2.2 in 0.5 mL of $CH_3CN$ and a small amount of water. The water was evaporated using a stream of nitrogen at 110° C. and co-evaporated to dryness with $CH_3CN$ (2×0.5 mL). The nitro precursor 8 (3.3 mg in 0.5 mL of DMSO) was added to the dried K[$^{18}$F] and the solution was heated at 120° C. for 15 minutes and then cooled to room temperature. $H_2O$ (10 mL) was added and the solution was passed through a $C_{18}$ Sep-Pak. The Sep-Pak was rinsed with water (5 mL×2) and the combined washings discarded. The crude product was eluted out from the $C_{18}$ Sep-Pak with $CH_2Cl_2$ (5 mL) and the solvent was evaporated to dryness. The residue was dissolved in 0.3 mL of EtOH and a saturated solution of $Cu(OAc)_2$—$H_2O$ (~20 mg) in 1 mL of EtOH was added, followed by $NaBH_4$ (~9 mg) in 0.8 mL of EtOH. The mixture was heated at 78° C. for 20 minutes, water (3 mL) was added and the mixture was filtered. The filtrate was extracted with $CH_2Cl_2$ (2 mL×3) and the combined organic layer was evaporated to dryness. The residue was dissolved in $CH_3CN$ (1.5 mL) and injected into a semi-preparative column (10×250 mm, Phenomenex Luna (2); $CH_3CN$:0.1 M $HCO_2NH_4$ (30:70) containing 0.3 v % of acetic acid, 5 mL/min). The fraction containing compound 12a was collected from 8–10 minutes and evaporated to dryness. To the residue 5 mL of normal saline was added and the resulting soltition was filtered through a 0.22 μm cellulose acetate membrane filter (Millipore) into a multi-injection vial. The radiochemical yield was 5–10% (decay corrected) and the synthesis time was 150 minutes from EOB. HPLC analysis showed that the radiochemical purity was >98% and the specific activity was 0.6 Ci/μmol.

Example 10

2-(5-Amino-4-chloro-2-nitro-phenylthio)-N,N-dimethyl-benzamide (18)

A solution of 2.5-dichloro-4-nitro-phenylamine (17) (3.0 g, 14.5 mmol) and 2-mercapto-N,N-dimethyl-benzamide (3.0 g, 16.6 mmol) in DMF (50 mL) was heated to reflux with potassium carbonate (10 g) for 24 h. The mixture was poured into ice water and the precipitate was collected by a filtration. A dark colored solid was recrystalized from petroleum ether/methylene chloride yielded 3.8 g of (18) as a pale yellow powder (75%): IR ($cm^{-1}$, KBr) 3461, 3376, 3153, 3154, 1627, 1575, 1492, 1135; $^1H$ NMR (200 MHz $CDCl_3$) δ 8.23 (s, 1H), 7.3–7.6 (m, 4H), 6.16 (s, 1H), 4.8 (br s, 2H), 3.37 (s, 3H), 2.86 (s, 3H). Anal. ($C_{15}H_{14}ClN_3O_3S$) C, H, N.

Example 11

2-(4-Chloro-5-fluoro-2-nitro-phenylthio)-N,N-dimethyl-benzamide (19)

To a solution of 2-(5-amino-4-chloro-2-nitro-phenylthio)-N,N-dimethyl-benzamide (18) (1 g, 2.84 mmol) in 6 N HCl (10 mL), a solution of sodium nitrite (0.3 g, 4.35 mmol) in wter (0.5 mL) was added at –5° C. (–0° C.). To this mixture, 48% hexafluorophosphoric acid (1.5 mL) was added at 0° C. and the mixture was stirred for 10 min. The precipitate was collected by filtration. The deep red solid was washed with ice water and air-dried using suction filter. The solid was further dried under high vacuum for several hours. The red powder was heated at 170° C. using oil bath until gas evolution was no longer observed. Dark colored residue was purified by silica gel chromatography to yield 380 mg of (19) (37%). IR ($cm^{-1}$, neat) 2927, 1634, 1521, 1465, 1400, 1336, 1282, 1249, 1091, $^1H$ NMR (200 MHz $CDCl_3$) δ 8.32 (d, J=2.8 Hz, 1H), 7.4–7.6 (m, 4H), 6.67 (d, J=5.0 Hz, 1H), 3.04 (s, 3H), 2.84 (s, 3H). Anal. ($C_{15}H_{12}ClFN_2O3S$) C, H, N.

Example 12

2-[(2-amino-4-chloro-5-fluorophenyl)thiol-N,N-dimethyl-benzenmethanamine (25)

To a solution of 2-(4-chloro-5-fluoro-2-nitro-phenylthio) N,N-dimethyl-benzamide (19) 200 mg, 0.56 mmol) in 10 mL anhydrous THF, 1N borane-THF complex (10 mL) was added at 0° C. under $N_2$. The mixture was heated to reflux for 2 h. After cooled down to 0° C., 1 mL of conc HCl was carefully added and the solvent was removed in vacuo. To the residue, 10 mL of water was added and the mixture was heated to reflux for 20 min. The mixture was cooled down and 1N NaOH was added to make pH of the solution basic (pH~10). Resulted cloudy aqueous solution was extracted with ethylacetate (5 mL×3). Combined organic liver was dried ($Na_2SO_4$) and the solvent was removed in vacuo. The residue was by sillca gel chromatography to yield 120 mg of 25 as colorless oil (68%): IR ($cm^{-1}$, neat) 3457, 3378, 3281, 2960, 2819, 2777, 1606, 1469, 1247, 1039, 747; $^1H$ NMR (200 MHz $CDCl_3$) δ 7.25 (m, 2H), 7.15 (m, 2H), 6.64 (m, 1H), 6.73 (d, J=6.6 Hz, 1H), 3.55 (s, 2H), 2.28 (s, 6H); HRMS calcd for $C_{15}H_{16}ClFN_2S$ (MH$^+$) 311.0786, found 311.0811. Anal. ($C_{15}H_{16}ClFN_2S$-2HCl-0.5H$_2$O) C, H, N.

Example 13

2-(4-Chloro-5-dimethylamino-2-nitro-phenylsulfanyl)-N,N-dimethyl-benzamide (22)

2-(5-Amino-4-chloro-2-nitro-phenylthio)-N,N-dimethyl-benzamide (18) (1.0 g, 2.84 mmol) was heated to reflux with methyl iodide 1.0 g) and potassium carbonate (5 g) in 10 mL of anhydrous DMF for 24 h. The mixture was poured into cold water and the precipitate was collected by filtration and purified by silica gel chromatography to yield 22 (Yellow powder, 0.7 g, 65%): IR (cm$^{-1}$, neat) 2923, 1636, 1577, 1498, 1322, 1299; $^1$H NMR (200 MHz CDCl$_3$) δ 8.23 (s, 1H), 7.4–7.6 (m, 4H), 6.20 (s, 1H), 3.04 (s, 3H), 2.82 (s, 3H), 2.71 (s, 6H). Anal. ($C_{17}H_{18}ClN_3O_3S$-0.5 H$_2$O) C, H, N.

Example 14

[2-Chloro-5-(2-dimethyaminocarbonyl-phenylthio)-4-nitro-phenyl]-trimethyl-ammonium trifluoromethanesulfonate (23)

2-(4-Chloro-5-dimethylamino-2-nitro-phenylsulfanyl)-N,N-dimethyl-benzamide (22) (0.5 g, 1.32 mmol) and methyl trifluoromethanesulfonate (0.3 g, 1.83 mmol) was heated to reflux in 5 mL of methylene chloride for 72 h. After cooled down, ethyl ether was added to the mixture. Precipitate was collected and recrystalized from CH$_2$Cl$_2$/ethylether repeatedly. Highly hygroscopic pale yellow powder was dried in vacuo and used directly for F-18 radiolabeling without further purifications (Yellow powder. 0.31 g, 40%): IR (cm$^-$, neat) 3060, 1623, 1553, 1519, 1256, 1154, 1027, 784, 640; $^1$H NMR (200 MHz CDCl$_3$) δ 8.53 (s, 1H), 7.74–7.90 (m, 4H), 7.69 (s, 1H), 3.69 (s, 9H), 3.40 (s, 3H), 3.06 (s, 3H); HRMS calcd for $C_{18}H_{21}{}^{35}ClN_3O_3S$ (M$^+$) 394.0992, found 394.0999.

Example 15

2-Chloro-5-(2-dimethylaminomethyl-phenylthio)-4-nitroaniline (20)

2-Chloro-5-(2-dimethylaminomethyl-phenylthio)-4-nitroaniline (20) was obtained from 2-(5-amino-4-chloro-2-nitro-phenylthio-N,N-dimethyl-benzamide (18) (0.5 g, 1.4 mmol) using the same procedure for the preparation of 25 (Light brown oil, 350 mg, 74%) IR (cm$^{-1}$, neat) 3449, 3376, 3068, 2969, 2821, 1617, 1579, 1548, 1494, 1285, 1251, 1135, 726; $^1$H NMR (200 MHz CDCl$_3$) δ 8.29 (s, 1H), 7.67 (d, J=6.6 Hz 1H), 7.54 (m, 2H), 7.34 (m, 1H), 4.54 (br s, 2H), 3.53 (s, 2H), 2.20 (s, 6H). Anal. ($C_{15}H_{16}ClN_3O_2S$-2HCl) C, H, N.

Example 16

2-(4-Chloro-5-fluoro-2-nitro-phenylthio)-N,N-dimethyl-benzenethanamine (21)

The desired product 21 was prepared from 20 (0.3 g 0.89 mmol) using the procedure for 4 (Colorless oil, 150 mg 50%): IR (cm$^{-1}$, neat) 2927, 2849, 1550, 1523, 1451, 1340, 1278, 732; $^1$H NMR (200 MHz CDCl$_3$) δ 8.22 (d, J=2.2 Hz, 1H), 7.3–7.6 (m, 4H), 6.62 (d, J=8.8 Hz, 1H), 3.52 (s, 2H), 2.18 (s, 6H). Anal. ($C_{15}H_{14}ClFN_2O_2S$—HCl) C, H, N.

Example 17

[F-18]2-[(2-Amino-4-chloro-5-fluorophenyl)thiol-N,N-dimethyl-benzenmethanamine[$^{18}$F]25

[$^{18}$F]Fluoride, produced by a cyclotron using $^{18}$O(p,n)$^{18}$F reaction, was directly injected to Sep-Pak Light QMA cartridge. The cartridge was dried by airflow and the activity was eluted with 2 mL of kryptofix 222 (K222)/K$_2$CO$_3$ solution (22 mg of K222 and 4.6 mg of K$_2$CO$_3$ in CH$_3$CN/H$_2$O 1.77/0.23). The solvent was removed at 110° C. under Argon stream. The residue was azeotropicaly dried with 1 ml anhydrous CH$_3$CN twice. A solution of precursor 7 (5 mg) in DMSO (0.5 mL) was added to the reaction vessel containing dried [F-18] activities. The solution was heated at 55° C. for 10 min. Water (2 mL) was added and the mixture was extracted with ethylacetete (1 mL×2). Combined organic layer was dried (Na$_2$SO$_4$) and the solvent was removed using Argon stream with gentle heating (55–60° C.). The residue was dissolved in CH$_2$Cl$_2$ (2 mL) and injected to Sep-Pac Plus silica cartridge. Cartridge was washed with 10 mL of CH$_2$Cl$_2$ and eluted activity was discarded. Retained activity was eluted with 5 ml CH$_2$Cl$_2$/ethylacetate 5/1. Solvent was removed using Argon stream with gentle heating. Compound 24 was obtained with a radiochemical purity of 100%. Compound 24 was dissolved in THF (0.5 mL) and 0.2 mL 1N BH$_3$-THF was added. The mixture was heated at 55° C. under argon for 25 min. Solvent was concentrated to near dryness by argon stream at the end of reaction. To this mixture, 0.4 mL of conc. HCl and 0.5 mL ethanol were added with external cooling. To the mixture, 1 mg of SnCl$_2$ was added and the reaction was kept at room temperature for 20 min. 5% NaOH (2 mL) was added to the reaction with cooling and extracted with ethylacetate (2 mL×2). Combined organic layer was filtered and dried (Na$_2$SO$_4$). The solvent was removed using argon stream. The residue was dissolved in CH$_2$Cl$_2$ (2 mL) and injected into Sep-Pac Plus Silica cartridge. The cartridge was washed with CH$_2$Cl$_2$/ethylacetate (20/1) 10 ml. Retained activity was eluted with ethylacetete/MeOH (2/1) 5 mL. The solvent was removed and [$^{18}$F]25 was obtained with RCP of 90%, which was further purified with HPLC (PRP-1 column, CH$_3$CN/dimethylglutarate buffer (pH 7) 9/1 1 mL /min rt=8.1 min) to attain RCP>99%. Entire procedure took approximately 3 h and radiochemical yield was 15% (decay corrected).

Example 18

Biological Evaluation:

In an in vitro binding assay using LLC-PK1 cells over expressing three different types of monoamine transporters (SERT, DAT or NET, respectively) and well-characterized ligands, [$^{125}$I]IPT and [$^{125}$I]IDAM, the binding affinity of each transporter was evaluated. Similar to that observed for the other phenylthiophenyl derivatives, IDAM, ADAM, DASB and MADAM, the target compound, 25 (ACF), displayed excellent binding affinity to SERT ($K_i$=0.05±0.01 nM). Binding affinities to the other monoamine transporters were more than 1000 fold lower, suggesting that ACF is highly potent and selective ligand tor SFRT. Two other nitro group containing intermediates, 18 and 21, also showed good binding affinity and selectivity. When the non-carrier added [$^{18}$F]ACF([$^{18}$F]25) was injected (iv) into rats, it showed excellent initial brain uptake (3.27±0.79% dose/organ, or 1.71±0.45 % dose/g). The tracer also localized in muscle, lungs and liver, organs where initial blood flow is high.

Regional distribution in the brain showed an expected high uptake and retention in striatum, hippocampus and hypothalamus regions, where the serotonin neurons were highly concentrated. It is also observed that the specific uptake for [$^{18}$F]ACF ([$^{18}$F]25), in the hypothalamus region reached the peak between 60–120 min after injection as compared to [$^{125}$I]ADAM, which reached the peak uptake at 4 h. The relatively fast kinetic of reaching peak uptake is highly desirable for future kinetic modeling studies. The ratio of hypothalamus/cerebellum was 3.53 at 60 min and slowly decreased with time. At 4 h after injection the ratio of hypothalamus/cerebellum was 2.37. To demonstrate that the uptake of [$^{18}$F]ACF ([$^{18}$F]25), in the retention in striatum, hippocampus and hypothalamus regions was related to selective serotonin transporters (SERT), rats were pretreated with specific monoamine transporter inhibitors (McN5652 for SERT; nisoxetine for NET and methylphenidate for DAT, respectively). There was significant change in the brain regioin where the serotonin neurons (serotonin transporter) were highly concentrated. There was a a significant decrease in specific retention at 60 min in the hypothalamus, striatum and hippocampus regions after the pretreatment of (+)McN5652 (2 mg/Kg at 5 min prior to tracer injection), suggesting that the [$^{18}$F]ACF ([$^{18}$F]25) was competing to the same SERT binding sites as those for (+)McN5652. No significant differences were observed in rats pretreated with nisoxetine or methylphenidate since these drugs are not binding to the SERT. The in vivo competition experiment strongly established that the binding of [$^{18}$F]ACF ([$^{18}$F]25), was directly related to the binding of SERT sites. In vivo metabolism of [$^{18}$F]ACF ([$^{18}$F]25), in three rats was evaluated at one hour after iv injection. It was found that essentially all of the activity (95.5±0.40% by HPLC analysis) extracted from the brain was the original [$^{18}$F]ACF ([$^{18}$F]25). The other tissues of organs showed more extensive metabolism, percentage of organic-extractable material were 6.76±1.00, 20.25±0.60 and 20.03±6.60 from plasma, kidney, and liver, respectively. It is likely that the metabolites in the peripheral tissue organs may not play an important role on uptake and retention of [18F]ACF in the brain of rats.

TABLE 1

Selectivity of compounds for monoamine transporters: SERT (serotonin transporter), DAT (dopamine transporter) or NET (norepinephrine transporter) ($K_I$, nM).

| Compound | SERT | DAT | NET |
| --- | --- | --- | --- |
| $R_1$ = NH$_2$ $R_2$ = F, 25(ACF) | 0.05 ± 0.01 | 3,020 ± 110 | 650 ± 80 |
| $R_1$ = NO$_2$ $R_2$ = NH$_2$, 18 | 2.39 ± 0.54 | 3,050 ± 860 | 15,050 ± 1060 |
| $R_1$ = NO$_2$ $R_2$ = F, 21 | 4.16 ± 0.33 | 31,900 ± 2503 | 2,810 ± 250 |

Values of the mean ± SEM of three determinations performed in duplicate. Cell membrane homogenates of LLC-PK1 cells overexpressing either SERT, NET or DAT. [$^{125}$I] IPT was used as the ligand for the DAT and NET assay. For the SERT binding assay, [$^{125}$I]IDAM was used.

TABLE 2

Organ distribution (% dose/organ) and brain regional uptake (% dose/g) of [$^{18}$F]ACF ([$^{18}$F]25) in rats (average 3 rates ± SD)

| Organ | 2 min | 30 min | 60 min | 120 min | 240 min |
| --- | --- | --- | --- | --- | --- |
| Blood | 6.56 ± 0.64 | 4.52 ± 0.22 | 4.65 ± 0.46 | 3.20 ± 0.57 | 2.33 ± 0.34 |
| Heart | 1.69 ± 0.24 | 0.18 ± 0.02 | 0.11 ± 0.01 | 0.06 ± 0.01 | 0.04 ± 0.01 |
| Muscle | 14.34 ± 9.76 | 10.70 ± 1.68 | 7.69 ± 0.29 | 4.02 ± 1.22 | 2.08 ± 0.05 |
| Lung | 14.89 ± 2.28 | 1.76 ± 0.20 | 0.73 ± 0.08 | 0.32 ± 0.06 | 0.15 ± 0.02 |
| Kidney | 6.97 ± 0.73 | 2.64 ± 0.79 | 1.38 ± 0.25 | 0.78 ± 0.15 | 0.51 ± 0.07 |
| Spleen | 0.64 ± 0.20 | 0.29 ± 0.09 | 0.13 ± 0.02 | 0.06 ± 0.02 | 0.03 ± 0.00 |
| Liver | 9.41 ± 1.82 | 15.20 ± 1.20 | 10.30 ± 2.50 | 5.90 ± 1.03 | 3.55 ± 0.35 |
| Skin | 4.76 ± 0.89 | 6.51 ± 0.66 | 5.97 ± 1.64 | 2.61 ± 0.17 | 1.53 ± 0.17 |
| Brain | 3.27 ± 0.79 | 1.28 ± 0.14 | 0.69 ± 0.09 | 0.21 ± 0.03 | 0.06 ± 0.01 |
| Bone | 0.01 ± 0.00 | 0.04 ± 0.03 | 0.08 ± 0.02 | 0.28 ± 0.06 | 0.27 ± 0.07 |

TABLE 2-continued

Organ distribution (% dose/organ) and brain regional uptake (% dose/g) of [$^{18}$F]ACF ([$^{18}$F]25) in rats (average 3 rates ± SD)

|  | 2 min | 30 min | 60 min | 120 min | 240 min |
|---|---|---|---|---|---|
| B. Regional brain distribution (% dose/g) | | | | | |
| Region | | | | | |
| Cerebellum | 1.33 ± 0.51 | 0.37 ± 0.07 | 0.15 ± 0.03 | 0.05 ± 0.01 | 0.02 ± 0.00 |
| Striatum | 1.78 ± 0.36 | 0.76 ± 0.08 | 0.45 ± 0.14 | 0.15 ± 0.02 | 0.05 ± 0.00 |
| Hippocampus | 1.60 ± 0.46 | 0.70 ± 0.06 | 0.45 ± 0.13 | 0.14 ± 0.02 | 0.04 ± 0.01 |
| Cortex | 2.31 ± 0.46 | 0.62 ± 0.07 | 0.33 ± 0.13 | 0.09 ± 0.01 | 0.03 ± 0.01 |
| Remainder | 1.69 ± 0.43 | 0.67 ± 0.09 | 0.39 ± 0.03 | 0.12 ± 0.01 | 0.03 ± 0.00 |
| Hypothalamus | 1.76 ± 0.48 | 0.85 ± 0.14 | 0.54 ± 0.13 | 0.17 ± 0.01 | 0.05 ± 0.00 |
| C. Ratio to Cerebellum | | | | | |
| Region | | | | | |
| Cerebellum | 1.00 ± 0.00 | 1.00 ± 0.00 | 1.00 ± 0.00 | 1.00 ± 0.00 | 1.00 ± 0.00 |
| Striatum | 1.41 ± 0.31 | 2.06 ± 0.19 | 2.88 ± 0.52 | 2.97 ± 0.16 | 2.35 ± 0.05 |
| Hippocampus | 1.24 ± 0.15 | 1.89 ± 0.24 | 2.91 ± 0.64 | 2.67 ± 0.15 | 1.99 ± 0.23 |
| Cortex | 1.84 ± 0.43 | 1.69 ± 0.20 | 2.10 ± 0.47 | 1.77 ± 0.04 | 1.52 ± 0.21 |
| Remainder | 1.32 ± 0.21 | 1.80 ± 0.11 | 2.56 ± 0.44 | 2.34 ± 0.09 | 1.58 ± 0.13 |
| Hypothalamus | 1.37 ± 0.19 | 2.29 ± 0.06 | 3.53 ± 0.33 | 3.23 ± 0.21 | 2.37 ± 0.23 |

TABLE 3

Effects of pretreatment with monoamine reuptake inhibitors on the specific binding of [$^{18}$F]ACF ([$^{18}$F]25) in rat brain regions.

| Region | Control | (+)McN5652 | Nisoxetine | Methylphenidate |
|---|---|---|---|---|
| Cerebellum | 0.21 ± 0.02 | 0.17 ± 0.03 | 0.19 ± 0.01 | 0.17 ± 0.02 |
| Striatum | 0.56 ± 0.09 | 0.25 ± 0.03* | 0.47 ± 0.03 | 0.47 ± 0.06 |
| Hippocampus | 0.53 ± 0.03 | 0.34 ± 0.06* | 0.46 ± 0.02 | 0.43 ± 0.03 |
| Cortex | 0.39 ± 0.03 | 0.24 ± 0.02* | 0.37 ± 0.04 | 0.35 ± 0.03 |
| Remainder | 0.48 ± 0.04 | 0.23 ± 0.01* | 0.41 ± 0.01 | 0.38 ± 0.05 |
| Hypothalamus | 0.63 ± 0.05 | 0.24 ± 0.03* | 0.55 ± 0.02 | 0.52 ± 0.07 |
| Whole brain | 0.81 ± 0.09 | 0.42 ± 0.02* | 0.74 ± 0.04 | 0.67 ± 0.04 |
| Blood | 0.26 ± 0.03 | 0.26 ± 0.03 | 0.26 ± 0.01 | 0.28 ± 0.02 |

B. Ratio to cerebellum

| Region | Control | (+)McN5652[+] | Nisoxetine[+] | Methylphenidate[+] |
|---|---|---|---|---|
| Cerebellum | 1.00 ± 0.00 | 1.00 ± 0.00 | 1.00 ± 0.00 | 1.00 ± 0.00 |
| Striatum | 2.63 ± 0.23 | 1.48 ± 0.32* | 2.50 ± 0.12 | 2.75 ± 0.09 |
| Hippocampus | 2.52 ± 0.13 | 1.93 ± 0.21* | 2.44 ± 0.11 | 2.50 ± 0.15 |
| Cortex | 1.86 ± 0.05 | 1.43 ± 0.27* | 1.94 ± 0.16 | 2.02 ± 0.21 |
| Remainder | 2.26 ± 0.03 | 1.37 ± 0.16* | 2.17 ± 0.04 | 2.23 ± 0.05 |
| Hypothalamus | 2.96 ± 0.03 | 1.36 ± 0.15* | 2.89 ± 0.11 | 3.05 ± 0.14 |

[+]Rats were pretreated with drugs with a dose of 2 mg/kg. iv. 5 min prior to the tracer administration (iv). One hour after the tracer in' e in each bra's compared between saline-injection. uptake in each region was compared Pretreated (coilti-01) and drug-pretreated rats. Values are presented as the average ± SD of three rats in each point.
*P < 0.05 (−)McN56-52 – serotonin transporter ligand; nisoxetine-norepinephrine transporter ligand; methylphenidate – dopamine transporter ligand.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I

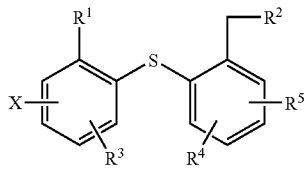

or a pharmaceutically acceptable salt thereof; wherein,
$R^1$ is selected from the group consisting of hydroxy($C_{1-4}$)alkyl, halo($C_{1-4}$)alkyl, nitro, azido, halo or —$NR^6R^7$ wherein,
  $R^6$ and $R^7$ are each independently selected from the group consisting of hydrogen, $C_{1-4}$ alkyl, halo($C_{1-4}$)alkyl, halo($C_{1-4}$)alkanoyl and halobenzoyl,
$R^2$ is —$NR^8R^9$ wherein,
  $R^8$ and $R^9$ are each independently selected from the group consisting of hydrogen, $C_{1-4}$ alkyl, halo($C_{1-4}$)alkyl, halo($C_{1-4}$)alkanoyl and halobenzoyl,
$R^3$ is independently selected from the group consisting of hydrogen, halo, cyano, $C_{1-4}$ alkyl, halo($C_{1-4}$)alkanoyl and ($C_{1-4}$)alkoxy,
$R^4$ and $R^5$ are each independantly selected from the group consisting of hydrogen, halo, cyano, $C_{1-4}$ alkyl, halo($C_{1-4}$)alkyl, halo($C_{1-4}$)alkanoyl and ($C_{1-4}$)alkoxy, and
X is hydrogen or halo, provided that:
one of $R^1$, $R^2$, $R^3$, $R^4$, $R^5$ or X contains $^{18}F$, and
if $R^1$ is —$NR^6R^7$ wherein $R^6$ and $R^7$ are both hydrogen, and
$R^2$ is —$NR^8R^9$ wherein $R^8$ and $R^9$ are both methyl, then
$R^3$ is hydrogen, halo, cyano, $C_{1-4}$ alkyl, or ($C_{1-4}$)alkoxy, and
if $R^1$ is fluoromethyl, then
$R^3$ and X are other than 4-iodine.

2. The compound of claim 1, wherein
$R^1$ is hydroxy($C_{1-4}$)alkyl,
one of $R^8$ and $R^9$ is $C_{1-4}$ alkyl the other of $R^8$ and $R^9$ is $C_{1-4}$ alkyl, halo($C_{1-4}$)alkyl, halo($C_{1-4}$)alkanoyl or halobenzoyl, and
X is hydrogen or halo.

3. The compound of claim 2, wherein
$R^1$ is hydroxymethyl,
one of $R^8$ and $R^9$ is methyl, the other of $R^8$ and $R^9$ is halo($C_{1-4}$)alkyl,
$R^3$, $R^4$ and $R^5$ are hydrogen, and
X is halo.

4. The compound of claim 1, wherein
$R^1$ is halo,
$R^8$ and $R^9$ are $C_{1-4}$ alkyl,
$R^3$, $R^4$ and $R^5$ are each hydrogen,
X is halo.

5. The compound of claim 1, wherein
$R^1$ is —$NR^6R^7$,
  $R^6$ and $R^7$ are independently selected from the group consisting of hydrogen, $C_{1-4}$ alkyl, halo($C_{1-4}$)alkyl, halo($C_{1-4}$)alkanoyl or halobenzoyl,
$R^8$ and $R^9$ are $C_{1-4}$ alkyl,
$R^3$, $R^4$ and $R^5$ are each independently selected from the group consisting of hydrogen, halo and cyano, and
X is hydrogen or halo, provided that:
if $R^6$ and $R^7$ are each hydrogen, then
$R^3$ and X are both hydrogen, or
$R^3$ is cyano, chloro, bromo or iodo, and
X is hydrogen or fluorine.

6. The compound of claim 5, wherein
$R^1$ is —$NR^6R^7$ wherein,
  $R^6$ and $R^7$ are independently selected from the group consisting of hydrogen, halo($C_{1-4}$)alkyl, halo($C_{1-4}$)alkanoyl or halobenzoyl,
$R^8$ and $R^9$ are each methyl,
$R^3$ is halo,
$R^4$ and $R^5$ are hydrogen, and
X is hydrogen.

7. The compound of claim 6 wherein,
$R^6$ and $R^7$ are independently selected from the group consisting of halo($C_{1-4}$)alkyl, halo($C_{1-4}$)alkanoyl or halobenzoyl.

8. The compound of claim 5 wherein,
$R^6$ and $R^7$ are hydrogen,
$R^8$ and $R^9$ are methyl,
$R^4$ and $R^5$ are each hydrogen,
$R^3$ is cyano, and
X is fluorine.

9. The compound of claim 5 wherein,
$R^3$ and X are each hydrogen,
$R^6$ and $R^7$ are hydrogen,
$R^8$ and $R^9$ are methyl,
$R^4$ is cyano, and
$R^5$ is $^{18}F$.

10. The compound of claim 5 wherein,
$R^6$ and $R^7$ are hydrogen,
$R^8$ and $R^9$ are methyl,
$R^4$ and $R^5$ are each hydrogen,
$R^3$ is halo, and
X is fluorine.

11. The compound of claim 10 wherein,
$R^3$ is 4-chloro, and
X is 5-$^{18}F$.

12. The compound of claim 1, wherein
$R^1$ is hydroxy($C_{1-4}$)alkyl,
$R^8$ and $R^9$ are each $C_{1-4}$ alkyl, and
$R^3$ is hydrogen or $C_{1-4}$ alkyl.

13. The compound of claim 12 wherein,
$R^4$ and $R^5$ are each hydrogen.

14. The compound of claim 1, wherein
$R^1$ is —$NH_2$,
one of $R^8$ and $R^9$ is hydrogen or $C_{1-4}$ alkyl, the other of $R^8$ and $R^9$ is $C_{1-4}$ alkyl, or halo($C_{1-4}$)alkyl,
$R^3$ is hydrogen or cyano,
$R^4$ and $R^5$ are hydrogen, and
X is hydrogen or halo, provided that,
if $R^8$ and $R^9$ are each $C_{1-4}$ alkyl, then
$R^3$ is other than cyano.

15. The compound of claim 14 wherein,
one of $R^8$ and $R^9$ is $C_{1-4}$ alkyl, the other of $R^8$ and $R^9$ is $C_{1-4}$ alkyl or halo($C_{1-4}$)alkyl.

16. The compound of claim 15 wherein,
one of $R^8$ and $R^9$ is $C_{1-4}$ alkyl, the other of $R^8$ and $R^9$ is halomethyl,
$R^3$ is hydrogen, $C_{1-4}$ alkyl, or cyano,
$R^4$ and $R^5$ are each hydrogen, and
X is halo.

17. The compound of claim 16, wherein
$R^8$ is methyl, and
$R^9$ is fluoromethyl.

18. The compound of claim 15, wherein
$R^8$ and $R^9$ are methyl,
$R^4$ and $R^5$ are each hydrogen,
$R^3$ is hydrogen, and
X is 4-$^{18}$F.

19. A pharmaceutical composition comprising a compound of claim 1, and
a pharmaceutically acceptable excipient or diluent.

20. A diagnostic composition for imaging serotonin transporters, comprising a compound of claim 1, and
a pharmaceutically acceptable excipient or diluent.

21. A method of imaging serotonin transporters in a mammal, comprising:
 a. introducing into a mammal a detectable quantity of a diagnostic composition of claim 20;
 b. allowing sufficient time for the labeled compound to be associated with serotonin transporters; and
 c. detecting the labeled compound associated with one or more serotonin transporters.

* * * * *